United States Patent [19]

Nathans et al.

[11] Patent Number: 6,020,189
[45] Date of Patent: Feb. 1, 2000

[54] FIBROBLAST GROWTH FACTOR HOMOLOGOUS FACTORS (FHFS) AND METHODS OF USE

[75] Inventors: Jeremy Nathans, Baltimore; Philip M. Smallwood, Woodbine, both of Md.

[73] Assignee: The Johns Hopkins University School of Medicine, Baltimore, Md.

[21] Appl. No.: 08/705,245

[22] Filed: Aug. 30, 1996

[51] Int. Cl.[7] .......................... C12N 15/11; C12N 15/63; C12N 15/85; C12N 1/21
[52] U.S. Cl. ................ 435/320.1; 435/325; 435/360; 435/252.3; 435/254.11; 536/23.51; 935/1; 935/2; 935/22; 935/66; 935/70; 935/72
[58] Field of Search ................ 536/23.51, 23.1; 935/23, 69–72, 66, 70, 22, 1, 2; 435/69.1, 320.1, 240.2, 325, 360, 252.3, 254.11

[56] References Cited

U.S. PATENT DOCUMENTS 5,773,252  6/1998  Greene et al. .

OTHER PUBLICATIONS

Boehringer Mannheim Biochemicals, 1991 Catalog p. 557.
Stratagene, 1991 Product Catalog, p. 66.
Gibco BRL Catalogue & Reference Guide, p. 292.
New England Biolabs, Catalog, 1986/87 pp. 60–62.
K. Ray and J. D. Robishaw, Cloning and sequencing of a rat heart cDNA encoding a G–protein B subunit related to the human retinal B3 subunit, Gene 149:337–340, 1994.
Bradbury et al. (1991) Proc. Natl. Acad. Sci. 88: 3353–3357, 1991.
Smallwood et al. (Sep., 1996) Proc. Natl. Acad. Sci. 93: 9850–9857, 1996.
Patry et al. (1994) FEBS Lett. 349: 23–39, 1994.
Riley et al. (1993) Development 118: 95–104, 1993.
Florkiewicz et al. (1995) J. Cell. Physiol. 162: 388–399, 1995.
Pizette et al. (1991) Cell Growth Diff. 2: 561–566, 1991.

*Primary Examiner*—Patricia A. Duffy
*Attorney, Agent, or Firm*—Gray Cary Ware & Freidenrich LLP; Lisa A. Haile

[57] ABSTRACT

The invention provides fibroblast growth factor homologous factor (FHF) polypeptides and nucleic acid molecules that encode them. Also included in the invention are diagnostic and therapeutic methods using FHF polypeptides and nucleic acids.

8 Claims, 24 Drawing Sheets

FIG. 1

| SEQ ID NO: 3 | hFHF-3 | M-AAHASSDI | RQKREVREPG | GSRPVSAQRR | VCPRGT-KSL | QQKQLLILLS | 48 |
| SEQ ID NO: 1 | hFHF-1 | MAAAIASSLI | RQKRQARESN | SDRVSASKRR | SSPSKDGRSL | QERHVLGVFS | 50 |
| SEQ ID NO: 4 | hFHF-4 | MAAAIASGLI | RQKRQAREQH | WDRPSASRRR | SSPSKN-RGL | QNGNLVDIFS | 49 |
| SEQ ID NO: 2 | hFHF-2 | MAAAIASSLI | RQKRQARERE | KSN--ACKCV | SSPSKG-KTS | QDKNKLNVFS | 47 |

| | hFHF-3 | KVRLCGGRPA | RPDRGPEPQL | KGIVTKLFCR | QGFYLQANPD | GSIQGTPEDT | 98 |
| | hFHF-1 | KVRFCSGRKR | PVERRPEPQL | KGIVTRLFSQ | QGYELQMHPD | GTIDGTKDEN | 100 |
| | hFHF-4 | KVTIFGLKKR | RLRRQ-DPQL | KGIVTRLYCR | QGYYLQMHPD | GALDGTKDDS | 98 |
| | hFHF-2 | RVKLFGSKKR | R-ERRPEPQL | KGIVTKLYSR | QGYHLQLQAD | GTIDGTKDED | 96 |

| | hFHF-3 | SSFTHFNLIP | VGLRVVHIQS | AKLGHYMAMN | AEGLLYSSPH | FTAEQRFKEC | 148 |
| | hFHF-1 | SDYTLFNLIP | VGLRVVAIQG | VKASIYMAMN | GEGYLYSSDV | FTPECKFKES | 150 |
| | hFHF-4 | TNSTKFNLIP | VGLTVVAIQG | VKTGIYIAMN | GEGYLYPSEL | FTPECKFKES | 148 |
| | hFHF-2 | STYTLFNLIP | VDLRVVAIQG | VQTKLYIAMN | SEGYLYISEL | FTPECKFKES | 146 |

| | hFHF-3 | VFENYYVIYA | SAIYRQRRSG | RAWYLGLCKE | GQVMKGNRVK | KIKAAAHELP | 198 |
| | hFHF-1 | VFENYYVIYS | STIYRQQESG | RAWFLGLNKE | GQIMKGNRVK | KIKPSSHFVP | 200 |
| | hFHF-4 | VFENYYVIYS | SMIYRQQESG | RAWFLGLNKE | GQAMKGNRVK | KIKPAAHFLP | 198 |
| | hFHF-2 | VFENYYVIHS | SMIYRQQSSG | RGWYLGLNKE | GEIMKGNHVK | KNKPAAHFLP | 196 |

| | hFHF-3 | KLLEVAMYQE | PSLHSVPEAS | PSS---PP-- | ---------- | -------AP | 225 |
| | hFHF-1 | KPIEVCMYRE | PSLHEIGE-- | -KQG--RSRK | SSGTPTMNGG | KVVNQ-DST | 243 |
| | hFHF-4 | KPLEVAMYRE | PSLHDVGETV | PKPGBYPSKS | TSASAIMNGG | KPVNKSKTT | 247 |
| | hFHF-2 | KPLKVAMYKE | PSLHDBGETV | RSGSGTPTKS | TSBSGBLNGG | KSMSHNEST | 245 |

FIG. 2A

|  | SEQ ID NO: |  |  |  |  |  |
|---|---|---|---|---|---|---|
| hFHF-1 | SEQ ID NO:1 | MAAAIASSLI | RQKRQARESN | SDRVSASKRR | SSPSKDGRSL | CERHVLVGFS 50 |
| hFHF-4 | SEQ ID NO:4 | MAAAIASGLI | RQKRQAREQH | WDRPSASRRR | SSPSKN-RGL | CNGNLVDIFS 49 |
| hFHF-2 | SEQ ID NO:2 | MAAAIASSLI | RQKRQARERE | KSN--ACKCV | SSPSKG-KTS | CDKNKLNVFS 47 |
| hFHF-3 | SEQ ID NO:3 | M-AALASSLI | RQKREVREPG | GSRPVSAQRR | VCPRGT-KSL | CQKQLILLS 48 |
| hFGF-9 | SEQ ID NO:9 | M-APLGE--V | GNYFGVQDAV | P------FGNVP | VLPVDS-PVL | ---LSDMLG 38 |
| hFGF-1 | SEQ ID NO:1 | M--AEGE--- | -------- | -------- | ITTFT ALTE----KF | ----NLP 19 |
| hFGF-2 | SEQ ID NO:2 | M--AAGS--- | -------- | -------- | ITTLP APLEDGGSG- | ----AFP 22 |
| hFHF-1 |  | KVRFCSGRKR | PVRRRPEPQL | KGIVTR--LF | SQQ-GYFLQM | HPDGTIDGTK 97 |
| hFHF-4 |  | KVRIFGLKKR | RLRRQ-DPQL | KGIVTR--LY | CRQ-GYYLQM | HPDGALDGTK 95 |
| hFHF-2 |  | RVKLFGSKKR | R--RRPEPQL | KGIVTK--LY | SRQ-GYHLQL | QADGTIDGTK 93 |
| hFHF-3 |  | KVRLCGGRPA | RPDRGPEPQL | KGIVTK--LF | CRQ-GFYLQA | NPDGSIQGTP 95 |
| hFGF-9 |  | QSEAGGLPRG | PAVTDLD-HL | KGILRRRQLY | CRT-GFHLEI | FPNGTQQGTR 86 |
| hFGF-1 |  | PGNY----K- | ----KPKL | ----LY | CSNGGMFLRI | LPDGTVDGTR 50 |
| hFGF-2 |  | PGHF----K- | ----DPKR | ----LY | CKNGGFFLRI | HPDGRVDGVR 53 |
| hFHF-1 |  | LIPVGLRVVA | IQGVKASLYC | AMNGEGYLYS | SDVFTPECKF 147 |
| hFHF-4 |  | LIPVGLRVVA | IQGVKTGLYI | AMNGEGYLYP | SELFTPECKF 145 |
| hFHF-2 |  | LIPVGLRVVA | IQGVQTKLYL | AMNSEGYLYT | SELFTPECKF 143 |
| hFHF-3 |  | LIPVGLRVVT | IRGVDSGLYL | GMNEKGELYG | SPHFTAECRF 145 |
| hFGF-9 |  | FISIAVGLVS | IRGBDSGLYL | SMNEKGELYG | SEKLTQECVF 136 |
| hFGF-1 |  | LSAESVGEVY | IKSTETGQYL | AMDTDGLLYG | SQTPNEECLF 100 |
| hFGF-2 |  | LQAEERGVVS | IKGVCANRYL | AMKEDGRLLA | SKCVTDECFF 103 |

FIG. 2B

```
hFHF-1  KESVFENYYV  IYSSTLYRQQ  ESGRAWFLGL  NKEGQIMKGN  RVKKTKPSSH  197
hFHF-4  KESVFENYYV  IYSSMLYRQQ  ESGRAWFLGL  NKEGQAMKGN  RVKKTKPAAH  195
hFHF-2  KESVFENYYV  TYSSMIYRQQ  QSGRGWYLGL  NKEGEIMKGN  HVKKNKPAAH  193
hFHF-3  KECVFENYYV  LYASALYRQR  RSGRAWYLGL  DKEGQVMKGN  RVKKTKAAAH  195
hFGF-9  REQFEENWYN  TYSSNLYKHV  DTGRRYYVAL  NKDGTPREGT  RTKRHQKFTH  186
hFGF-1  LERLEENHYN  TYISKKHAEK  ----NWFVGL  KKNGSCKRGP  RTHYGQKAIL  146
hFGF-2  FERLESNNYN  TYRSRKYT--  ----SWYVAL  KRTGQYKLGS  KTGPGQKAIL  147 hFHF-1  FVPKPIEVCM  YREPSLHEIG  E---KQG--R  SRKSSGTPTM  NGGKVVNQ-D  241
hFHF-4  FLPKPLEVAM  YREPSLHDVG  ETVPKPGVTP  SKSTSASAIM  NGGKPVNKSK  245
hFHF-2  FLPKPLKVAM  YKEPSLHDLT  EFSRSGSGTP  TKSRSVSGVL  NGGKSMSHNE  243
hFHF-3  FLPKLLEVAM  YQEPSLHSVP  EASPSS---P  P-------          223
hFGF-9  FLPRPVDPD-  --KVPELY--                              206
hFGF-1  FLPLPVS---                                          153
hFGF-2  FLPMSAKS--                                          155 hFHF-1  ST                                                  243
hFHF-4  TT                                                  247
hFHF-2  ST                                                  245
hFHF-3  AP                                                  225
hFGF-9  QS                                                  208
hFGF-1  SD                                                  155
hFGF-2  --                                                  155
```

FIG. 3A

$$\underbrace{\begin{array}{l}\text{SEQ ID NO: 17}\\\text{SEQ ID NO: 12}\\\text{SEQ ID NO: 14}\\\text{SEQ ID NO: 15}\\\text{SEQ ID NO: 13}\\\text{SEQ ID NO: 16}\\\text{SEQ ID NO: 9}\\\text{SEQ ID NO: 2}\\\text{SEQ IH NO: 11}\\\text{SEQ ID NO: 4}\\\text{SEQ ID NO: 8}\\\text{SEQ ID NO: 1}\\\text{SEQ ID NO: 10}\\\text{SEQ ID NO: 3}\\\text{SEQ ID NO: 7}\\\text{SEQ ID NO: 6}\\\text{SEQ ID NO: 5}\end{array}}_{*}$$

FIG. 3B

| | | | | | | |
|---|---|---|---|---|---|---|
| mFGF-8 | MGSRPS---- | ---------- | ---------- | ---------- | T------QHVR | 37 |
| mFGF-3 | MGLIWLLLL- | ---------- | ---------- | ---------- | -------RDA- | 29 |
| hFGF-5 | MSLSFLLLLF | --SLLEPSW- | ---------- | -PT------- | ---------- | 50 |
| hFGH-6 | MRSGAGRLQ- | FSHLILSAWA | HGEKRLAPKG | QPGPAATDRN | PIGSSSRQSS | 47 |
| hFGF-4 | MSGPGTAAV- | --GTLWA--L | VFLGILVGMV | -TGPGTRLR- | NTLLD-SRGW | 47 |
| hFGF-17 | M-HKWIL--- | -ALLPAVLL | ALLAPWAGRG | VPSPAGTRAN | YLEARLRTTW | 39 |
| mFGF-2 | MTAAIAS--- | -TWILPTLL | -TRSCFHIIC | GAAAPTAPNG | DMT----PEQ- | 38 |
| mFHF-2 | MAAAIAS--- | ---------- | -SLIRQKRQ | LVGTISLACN | G-------KTSC | 38 |
| mFHF-4 | MAAAIAS--- | ---------- | -SLIRQKRQ | ACKCVSSPSK | G-------KTSC | 40 |
| mFHF-4 | MAAAIAS--- | ---------- | -GLIRQKTQ | ACKCVSSPSK | N-------RGLF | 40 |
| mFHE-1 | MAAAIAS--- | ---------- | -GLIRQKRQ | AREREKSN-- | N-------RGLC | 41 |
| mFHE-1 | MAAAIAS--- | ---------- | -SLIRQKRQ | AREREKSN-- | D-------GRSLC | 41 |
| hFHF-3 | M-AALAS--- | ---------- | -SLIRQKRE | AREQHWDRPS | D-------GRSLC | 39 |
| hFHE-3 | M-AALAS--- | ---------- | -SLIRQKRE | AREQHWDRPS | T-------KSLC | 39 |
| mFGF-9 | M-APLGE--- | ---------- | --VGNYFG | AREQNSDRVS | T-------KSLC | 32 |
| hFHE-2 | MAAFSIT--- | ---------- | --TL----- | AREQNSDRVS | ---------PVL- | 19 |
| hFGF-1 | MAEGEIT--- | ---------- | --TF----- | BREPGGSRPV | ---------GSG- | 16 |
| | | | | SAQRRVCPRG | | |
| | | | | SAQRRBCPRG | | |
| | | | | FGNVPVLPVD | | |
| | | | | ---------- | | |
| | | | | PALPED---- | | |
| | | | | TALTE----- | | |

*

| | | | | | | |
|---|---|---|---|---|---|---|
| mFGF-8 | E------QSLVT | DQL------- | ---SRR | LIRTYQ---- | LYSR-TSGKH | 64 |
| mFGF-3 | ---------- | --------GGR | GGVYEHLG-- | -GAPRRR--K | LYC--ATKYH | 55 |
| hFGF-5 | SSAMSSSAS | SSPAASLGSQ | GSGLEQSSFQ | WSPSGRRTGS | LYCRVGIGFH | 100 |
| hFGH-6 | GTL--LSRSR | AGLAGE--IA | GVNWESG-YL | VGIKRQR--R | LYCNVGIGFH | 87 |
| hFGF-4 | ESLVALSLAR | LPVAAQPKEA | AVQSGAGDYL | LGIKRLR--R | LYCNVGIGFH | 95 |
| hFGF-17 | --MATNV | NCSSPERHTR | SYDYMEG--- | -GDIRVR--R | LFCRTQWYLR | 78 |
| mFGF-2 | DKNKLNVFSR | VKLFGSKKRR | -RRRPEPQ-L | KGIV-TK-- | LYSR-Q-GYH | 80 |
| mFHF-2 | DKNKLNVFSR | VKLFGSKKRR | -RRRPEPQ-L | KGIV-TK-- | LYSR-Q-GYH | 80 |
| mFHF-4 | NGNLVDIFSK | VRIFGLKKRR | -LRRQDPQ-L | KGIV-TR-- | LYCR-Q-GYY | 82 |
| mFHF-4 | NGNLVDIFSK | VRIFGLKKRR | -LRRQDPQ-L | KGIV-TR-- | LYCR-Q-GYY | 82 |
| mFHE-1 | ERHVLGVFSK | VRFCSGRKRP | VRRRPEPQ-L | KGIV-TR-- | LFSQ-Q-GYF | 84 |
| hFHE-1 | ERHVLGVSFK | VRFCSGRKRP | VRRRPEPQ-L | KGIV-TR-- | LFSQ-Q-GYF | 84 |

FIG. 3C

```
mFHF-3  QKQLLILLSK VRLCGGRPTR QDRGPEPQ-L KGIV-TK--- ---------- LFCR-Q-GFY  82
hFHF-3  QKQLLILLSK VRLCGGRPAR PDRGPEPQ-L KGIV-TK--- ---------- LFCR-Q-GFY  82
hFGF-9  ---LSDHLGQ SEAGGLPRGP AVTDLD-H-L KGIL-RRRQ- ---------- LYCR-T-GFH  73
hFGF-2  ----AFPP GHF------- -------- ---KDPK-R- ---------- LYCK-NGGFF  40
hFGF-1  ----NLPP GNY------- -------- ---KKPK-L- ---------- LYCS-NGGHF  37 mFGF-8  VQVLANKRIN AMAEDGSPFA KLIVETDTFG SRVRVRGAET GLYICMNKKG 114
mFGF-3  EQLHPSGRVN GS-LENSAYS ILEITABEBG V-VAIKGLFS GRYLAMNKPG 103
hFGF-5  EQIYPDGKBN GS-HEAMNLS VLEIFABSQG I-VGIRGVFS NKFLAMSKKG 148
hFGF-6  EQVLPDGRIS GT-HEENPYS LLEISTBERG V-VSLFGVRS ALEBAMNSKG 135
hFGH-4  EQALPDGRIG GA-HADTRDS LLELSPBERG V-VSIFGVAS RFEVAMNSKG 143
hFGF-7  IDKRGKVK-G TQ-EMKNNYN IMEIRTVAVG I-VAIKGVES EFYLAMNSEG 125
mFHF-2  LQLQADGTID GTKDEDSTYT LFNLIPVGLR V-VAIQGVQT KLYLAMNSEG 129
hFHF-2  LQLQADGTID GEKDEDSTYT LFNLIPVGLR V-VAIQGVQT KLYLAMNSEG 129
mFHF-4  LQMPHDGALD GTKDDSTNST LFNLIPVGLR V-VAIQGVKT GLYIAMNDED 131
hFHF-4  LQMPHDGALD GTKDDSTNST LFNLIPVGLR V-VAIQGVKT GLYIAMNEG 131
mFHF-1  LEMHPDGTID GTKDENSDYT LFMLIPVGLR V-VAIQGVKA SLTAAMNGEG 133
hFHF-1  LQMGPDGTID GTKDENSDYT LFNLIPVGLR V-VAIQGVKA SLYVAMNGEG 133
mFHF-3  LQANPDGSIQ GTPEDTSSFT HFNLIPVGLR V-VTIQSAKL GHYMAMNGEG 133
hFHF-3  LQANPDGSIQ GTRKDHSRFG HFNLIPVGLR V-VTIQSAKL GHYMAMNAEG 131
mFGF-3  LEIFPNGTIQ GTRKDHSRFG ILEFISIAVG L-VSIRGVDS GLYLGMNEKG 131
hGFG-9  LRIHPDGRVD GVREKSDPHI KLQQAEERG V-VSIKGVCA NRYLAMKEDG 122
hHGH-2  LRILPDGTVD GTRDRSDQHI QLQLSAESVG E-VYIKSTET GQYLAMDTDG  89
hFHF-1                                                              86 mFGF-8  KLIALSNGKG KDCVEIEIBL ENNYTALQNA KYE------- --------G 148
mFGF-3  RLYASDHYN- AECEEFVERIH ELGYNTYASR LYRTGSSGPG AQRQPGAQRP 152
hFHF-5  KLHASAKFT- DDCKFPERFQ ENSYNTYASA IHRTEKTG-- ---------- 187
hFGF-6  RLYATPSFQ- EECKFRETLL PNNYNAYESD LYQGT----- ---------- 169
hFGF-4  KLYGSPFFT- DECIEKEILL PNNYNAYESY KYPGM----- ---------- 177
hFGF-7  KLYAJJECN- EDCNEKELIL INHYNTYASA KWTHNGG--- ----------E 162
```

FIG. 3D

```
mFHF-2  YLYTSEHGY- PECKFKESBF ENYVTYSSM IYRQQQSG- ---------- RG 168
hFHF-2  YLYTSELFT- PECKFKESVF ENYVTYSSM IYRQQQSG- ---------- RG 168
mFHF-4  YLYPSELFT- PECKFKESVF ENYVIYSSM LYRQESG-- ---------- RA 170
hFHF-4  YLYPSELFT- PECKFKESVF ENYVIYSSM LYRQQESG- ---------- RA 170
mFHF-1  YLYSSDVFT- PECKFKESVF ENYVIYSST LYRQQESG- ---------- RA 172
hFHF-1  YLYSSDVFT- PECKFKESVF ENYVIYSST LYRQQESG- ---------- RA 172
mFHF-3  LLYSSPHFT- PECKFKESVF ENYVVLYASA LYRQRRSG- ---------- RA 170
hFHF-9  ELYGSEKLT- AECREKECVF ENWYNTYSSN LYRQRRSG- ---------- RR 161
hFGF-2  RLLASKCVT- QECFFFERLE SNNYNTYRSR KYT------ ---------- -S 122
hFGF-1  LLYGSQTPN- EECLFLERLE ENHYNTYISK KHAEK---- ---------- -N 121 mFGF-8  WYMAETRKGR PRKGSKTRQH Q-------- RE--VHFMKR LPRGHHTTEQ  187
mFGF-3  WYVSVNGKGR PRRGFKTRRT QKSSLFLPRV LGHKDHEMVR LLQSSQPRAP  202
hFGF-5  WYVALNKPGK AKRGCSPR-- VK------- IS--THFLPR FKQSEQPELS  228
hFGF-6  -YIALSKYGR VKRGSKVS-- ---------  TV--THFLPR I--------  198
hFGF-4  -EIALSKNGK TKKGNRVS-- ---------  KV--THFLPR L--------  206
mFHF-7  MFVALNQKGI PBPGKKTKKE QK------- -T--AHELPR A--------  192
mFHF-2  WYLGLNKEGE IMKGNHBKKN K-------- PA--AHELPK PLKVAMYKEP  207
hFHF-2  WYLGLNKEGE IMKGNHVKKN K-------- PA--AHELPK PLKVAMYKEP  207
mFHF-4  WFLGLNKEGE IMKGNRVKKT K-------- PA--AHELPK PLEVAMYREP  209
hFHF-4  WFLGLNKEGE AMKGNRVKKT K-------- PA--AHELPK PLEVAMYREP  209
mFHF-1  WFLGLNKEGE IMKGNRVKKT K-------- PS--SHEVPK PIEVCMYREP  211
hFHF-1  WELGLNKEGE VMKGNRVKKT K-------- PS--SHEVPK PIEVCMYREP  211
mFHF-3  WYLGLDKEGR VMKGNRVKKT K-------- AA--AHEVPK LLEVAMYREP  209
hFHF-3  WYLGLDKEGQ VMKGNRVKKT K-------- AA--AHELPK LLEVAMYQEP  209
hFGF-9  YYVALNKDGT PREGTRTKRH Q-------- KF--THELPR PVDPD--KVP  198
hFGF-2  WYVALKRTGQ YKIGSKTGPG Q-------- KA--ILELPM SAKS------  155
hFGF-1  WFVGLKKNGS CKPGPRTHYG Q-------- KA--ILELPL PVS-------  153
```

FIG. 3E

```
mFGF-8  SLR--FEELN YP---PFTR- ---------- ------S LRGSQRTWAP EPR  215
mFGF-3  GEGSQPRQRR QKKQSPGDHG KMETLSTRAT ---------- PSTQLHTGGL AVA  245
hFGF-5  FTVTVP---E KKNPPSPIKS KIPLSAPRKN ---------- TNSVKYRLKF RFG  268
hFGF-6  ---------- ---------- ---------- ---------- ---------- ---  198
hFGF-4  ---------- ---------- ---------- ---------- ---------- ---  206
hFGF-7  ---------- ---------- ---------- ---------- ---------- -IT  194
mFHF-2  SLHDLTEFSR SGSGTPTKSR ---------- SVSGV LNGGKSMSHN EST  245
hFHF-2  SLHDLTEFSR SGSGTPTKSR ---------- SVSGV LNFFKSMSHN EST  245
mFHF-4  SLHDVGETVP KAGVTPSKST ---------- SASAI MNGGKPVNKC KTT  247
hFHF-4  SLHDVGETVP KPGVTPSKST ---------- SASAI MNGGKPVNKS KTT  247
mFHF-1  SLHEIGE--- KQG--RSRKS ---------- SGTPT MNGGKVVNQ- DST  243
hFHF-1  SLHEIGE--- KQG--RSRKS ---------- SGTPT MNGGKVVNQ- DST  243
mFHF-3  SLHSVPETSP SS---PP--- ---------- ----- --------- -AH  225
hFHF-3  SLHSVPEASP SS---PP--- ---------- ----- --------- -AP  225
hFGF-9  ELY------- KD-------- ---------- --I-- -LS------ -QS  208
hFGF-2  ---------- ---------- ---------- ---------- ---------- ---  155
hFGF-1  ---------- ---------- ---------- ---------- ---------- -SD  155
```

FIG. 5A

```
SEQ ID NO:18
GAATTCCGCA CACTGCGTTC GGGGTACCAA GTGGAAGGGG AAGAACGATG CCCAAAATAA    60
CAAGACGTGC CTGGGACCGC CCCGCCCCGC CCCCCGGCCG CCAGAGGTTG GGGAAGTTTA   120
CATCTCCATT TTCACACATT TTGTCGCCAC ATACTGCAGC TGCCCAGACT TTGACTAACC   180
CGGGTTTTCG ATACTGCAGC CTCCTCAAAT TTTAGCACTG CCTCCCCGCG ACTGCCCTTT   240
CCCTGGCCGC CCAGGTCCTG CCCTCGCCCC GGCGGAGCGC AAGCCGGAGG GCGCAGTAGA   300
GGCTGGGGCC TGAGGCCCTC GCTGAGCAGC TATGGCTGCG GCGATAGCCA GCTCCTTGAT   360
                                          M  A  A  A  I  A  S  S  L  I
SEQ ID NO:1
CCGGCAGAAG CGGCAGGCGA GGGAGTCCAA CAGCGACCGA GTGTCGGCCT CCAAGCGCCG   420
 R  Q  K    R  Q  A    R  E  S  N  S  D  R   V  S  A    S  K  R  R
CTCCAGCCCC AGCAAAGACG GGCGCTCCCT GTGCGAGAGG CACGTCCTCG GGGTGTTCAG   480
 S  S  P    S  K  D    G  R  S  L  C  E  R   H  V  L    G  V  F  S
CAAAGTGCGC TTCTGCAGCG GCCGCAAGAG GCCGGTGAGG CGGAGACCAG AACCCCAGCT   540
 K  V  R    F  C  S    G  R  K  R  P  V  R   R  R  P    Q  P  Q  L
CAAAGGGATT GTGACAAGGT TATTCAGCCA GCAGGGATAC TTCCTGCAGA TGCACCCAGA   600
 K  G  I    V  T  R    L  F  S  Q  Q  G  Y   F  L  Q    M  H  P  D
TGGTACCATT GATGGGACCA AGGACGAAAA CAGCGACTAC ACTCTCTTCA ATCTAATTCC   660
 G  T  I    D  G  T    K  D  E  N  S  D  Y   T  L  F    N  L  I  P
CGTGGGCCTG CGTGTAGTGG CCATCCAAGG AGTGAAGGCT AGCCTCTATG TGGCCATGAA   720
 V  G  L    R  V  V    A  I  Q  G  V  K  A   S  L  Y    V  A  M  N
TGGTGAAGGC TATCTCTACA GTTCAGATGT TTTCACTCCA GAATGCAAAT TCAAGGAATC   780
 G  E  G    Y  L  Y    S  S  D  V  F  T  P   E  C  K    F  K  E  S
TGTGTTTGAA AACTACTATG TGATCTATTC TTCCACACTG TACCGCCAGC AAGAATCAGG   840
 V  F  E    N  Y  Y    V  I  Y  S  S  T  L   Y  R  Q    Q  E  S  G
```

FIG. 5B

```
SEQ ID NO:1(CONT'D)
CCGAGCTTGG TTTCTGGGAC TCAATAAAGA AGGTCAAATT ATGAAGGGGA ACAGAGTGAA    900
 R  A  W   F  L  G     L  N  K  E   G  Q  I    M  K  G    N  R  V  K
GAAACCAAG CCCTCATCAC ATTTGTACC GAAACCTATT GAAGTGTGTA TGTACAGAGA      960
 K  T  K   P  S  S    H  F  V  P   K  P  I    E  V  C    M  Y  R  E
ACCATCGCTA CATGAAATTG GAGAAAAACA AGGGCGTTCA AGGAAAAGTT CTGGAACACC   1020
 P  S  L   H  E  I    G  E  K  Q   G  R  S    R  K  S    S  G  T  P
AACCATGAAT GGAGGCAAAG TTGTGAATCA AGATTCAACA TAGCTGAGAA CTCTCCCCTT   1080
 T  M  N   G  G  K    V  V  N  Q   D  S  T
CTTCCCTCTC TCATCCCTTC CCCTTCCCATT TACCCATTTC CTTCCAGTAA             1140
ATCCACCCAA GGAGAGGAAA ATAAAATGAC CTAGTGGCTA AGATTCTGCA              1200
CTCAAAATCT TCCTTTGTGT AGGACAAGAA AATTGAACCA AAGCTTGCTT GTTGCAATGT   1260
GGTAGAAAAT TCACGTGCAC AAAGATTAGC ACACTTAAAA GCAAAGGAAA AAATAAATCA   1320
GAACTCCATA AATATTAAAC TAAACTGTAT TGTTATTACG AGAAGGCTAA TTGTAATGAA   1380
GACATTAATA AAGATGAAT AAACTTATTA CTTTCGGAAT TC
```

FIG. 6A

```
SEQ ID NO:19
AATTCCGCTT GCACAGTGTC CGCCGGGCGC CGCCGGGCGAC AGGGGCCGAC CGCACGCAGT CGCGCAGTTC    60
TGCCTCCGCC TGCCAGTCTC GCCCCGCGATC GCCCCGCGGG CCGGCCCGGG GCTGTGGCGT CGACTCCGAC   120
CCAGGCAGCC AGCAGCCCCGC GCGGGAGCCG GACCGCCCGC GACCGCCCGC GAGGGAGCTG CCACGGCATG   180
CTGAGCCCCC TCCTTGGCTG AAGCCCGAGT GCGGAGAAGC GCGGGCAAAC GCAGGCTAAG   240
GAGACCAAAG CGGCGAAGTC GCGAGACAGC GGACAAGCAG GCCACCACAA GGAGGAGGAG   300
GCGAACCCAG AGAGGGGCAG CAAAAGAAGC GGTGGTGGTG GGCGTCGTGG CCATGGCGGC   360

SEQ ID NO:2
GGCTATCGCC AGCTCGCTCA TCCGTCAGAA GAGGCAAGCC CGCGAGCGCG AGAAATCCAA   420
 A   I   A   S   S   L   I   R   Q   K   R   Q   A   R   E   R   E   K   S   N
CGCCTGCAAG TGTGTCAGCA GCCCCAGCAA AGGCAAGACC AGCTGCGACA AAAACAAGTT   480
 R   L   Q   C   V   S   S   P   S   K   G   K   T   S   C   D   K   N   K   L
AAATGTCTTT TCCCGGGTCA AACTCTTCGG CTCCAAGAAG AGGCGCAGAA GAAGACCAGA   540
 N   V   F   S   R   V   K   L   F   G   S   K   K   R   R   R   R   P   E
GCCTCAGCTT AAGGGTATAG TTACCAAGCT ATACAGCCGA CAAGGCTACC ACTTGCAGCT   600
 P   Q   L   K   G   I   V   T   K   L   Y   S   R   Q   G   Y   H   L   Q   L
GCAGGCGGAT GGAACCATTG ATGGCACCAA AGATGAGGAC AGCACTTACA CTCTGTTTAA   660
 Q   A   D   G   T   I   D   G   T   K   D   E   D   S   T   Y   T   L   F   N
CCTCATCCCT GTGGGTCTGC GAGTGGTGGC TATCCAAGGA GTTCAAACCA AGCTGTACTT   720
 L   I   P   V   G   L   R   V   V   A   I   Q   G   V   Q   T   K   L   Y   L
AGAAGAAC ACTTGTACAC CTCGGAACTT TTCACACCTG AGTGCAAATT   780
 A   M   N   S   E   G   Y   L   Y   T   S   E   L   F   T   P   E   C   K   F
CAAAGAATCA GTGTTTGAAA ATTATTATGT TCAATGATAT ACCGTCAGCA   840
 K   E   S   V   F   E   N   Y   Y   V   S   M   I   Y   R   Q   Q
```

FIG. 6B

```
SEQ ID NO:2 (CONT'D)
GCAGTCAGGC CGAGGGTGGT ATCTGGGTCT GAACAAAGAA GGAGAGATCA TGAAAGGCAA   900
 Q  S  G   R  G  W    Y  L  G  L   N  K  E    G  E  I    M  K  G  N
CCATGTGAAG AAGAACAAGC CTGCATCTCA TTTTCTGCCT AAACCACTGA AAGTGGCCAT   960
 H  V  K   K  N  K    P  A  H     F  L  P    K  P  L    K  V  A  M
GTACAAGGAG CCATCACTGC ACGATCTCAC GGAGTTCTCC CGATCTGGAA GCGGGACCCC  1020
 Y  K  E   P  S  L    H  D  L  T  E  F  S    R  S  G    S  G  T  P
AACCAAGAGC AGAAGTGTCT CTGGCGTGCT GAACGGAGGC AAATCCATGA GCCACAATGA  1080
 T  K  S   R  S  V    L  G  V  L  N  G  G    K  S  M    S  H  N  E
ATCAACGTAG CCAGTGAGGG CAAAAGAAGG GCTCTGTAAC AGAACCTTAC CTCCAGGTGC  1140
TGTTGAATTC
```

FIG. 7A

```
SEQ ID NO:20
GAATTCCGGC TCTTGGGGAG CCCAGCGCGC TCCGGGCGCC TCCGGGTTTG GGGGTGTCTC    60
SEQ ID NO:3
CGAGCCCGGG GCTATGGCGG CGCTGGCCAG CCCAGCGCGC CGGCAGAAGC GGAGGTCCG   120
             M  A     A  L  A  S    P  A  R    R  Q  K    E  V  R
GTCCCTTTGC GGCAGCCCGG CAGAAGCAGC CGGTGTCGGC GTGTGTCCCC GCGGCACCAA   180
 V  P  L   C  G  S  R  Q  K  Q    P  V  S  A  V  C  P    R  G  T  K
CCGCGCGCGG CCGGACCGCG GTCCCTTTGC TCCTCATCCT GCTGTCCAAG GTGCGGACTGT   240
 P  A  R   P  D  R    S  L  C  S  L  I  I  L  L  S  K   V  R  L V
GCCGCCAGCG GGTTCTACC CCCGGAGCC TCAGCTCAAA GGCATCGTCA CCAAAACTGTT   300
 A  A  S   G  F  Y    P  E  P    L  S  S  K   G  I  V    T  K  L  F
CTGCCGCCAG GGTTTCTACC GCCCGGAGCC TCAGCTCAAA TCCCGACGGA GCATCCATGA GCACCCCAGA   300
 C  R  Q   G  F  Y    L  Q  A  N   L  H  N  L  I  P  V   G  T  P  E
GGATACCAGC TCCTTCACCC ACTTCAACCT GATCCCTGTG GGCCTCCGTG TGGTCACCAT   420
 D  T  S   S  F  T    L  H  N  L   I  P  V    G  L  R    V  V  T  I
CCAGAGCGCC AAGCTGGGTC ACTACATGGC CATGAATGCT GAGGGACTGC TCTACAGTTC   480
 Q  S  A   K  L  G    H  Y  M  A   M  N  A    E  G  L    L  Y  S  S
```

FIG. 7B

```
SEQ ID NO:3
GCCGCATTTC ACAGCTGAGT GTCGCTTTAA GGAGTGTGTC TTTGAGAATT ACTACGTCCT   540
 P  H  F    T  A  E     C  R  F  K   E  C  V     F  E  N  Y    Y  V  L
GTACGCCTCT GCTCTCTACC GCCAGCGTCG TTCTGGCCGG GCCTGGTACC TCGGCCTGGA   600
 Y  A  S    A  L  Y     R  Q  R  R   S  G  R     A  W  Y     L  G  L  D
CAAGGAGGGC CAGGTCATGA AGGGAAACCG AGTTAAGAAG ACCAAGGCAG CTGCCCACTT   660
 K  E  G    Q  V  M     K  G  N  R   V  K  K     T  K  A  A   A  H  F
TCTGCCCAAG CTCCTGGAGG TGGCCATGTA CCAGGAGCCT TCTCTCCACA GTGTCCCCGA   720
 L  P  K    L  L  E  V   A  M  Y     Q  E  P   S  L  H  S     V  P  E
GGCCTCCCCT TCCAGTCCCC CTGCCCCCTG AAATGTAGTC CCTGGACTGG AGGTTCCCTG   780
 A  S  P    S  S  P     P  A  P
CACTCCCCAGT GAGCCAGCCA CCACCACAAC CTGTCTCCCA GTCCTGCTCT CACCCCTGCT   840
GCCACACACA TGCCCTGAGC AGCCAGGTGG CACTAGGTGC TCTACCCTGA GGGAGCCTAG   900
GGGCTGACTG TGACTTCCGA GGCTGCTGAG ACCCTTAGAT CTTTGGGCCT AGGAGGGAGT   960
C
```

FIG. 8A

```
SEQ ID NO:21
CGGCCGCCTTC CCCTTCCGGTG CCCCCGGCTC GCCGTCCTCC CGCGCCCTCC GCCGCCCTCG CTCCCCGGAC    60
CCGTTCCCGG GGCCACCATG GCCGCGGCCA TCGCTAGCGG CTTGATCCGC CAGAAGCGGC  120
                     M  A  A  A  I  A  S  G  L  I  R  Q  K  R

SEQ ID NO:4
AGGCGCGGGA GCAGCACTGG GACCGGCCGT CTGCCAGCAG GAGGCGGAGC AGCCCCAGCA  180
 Q  A  R  E  Q  H  W  D  R  P  S  A  S  R  R  R  S  Q  P  S
AGAACCGCGG GCTCTGCAAC GGCAACCTGG TGGATATCTT CTCCAAAGTG CGCATCTTCG  240
 K  N  R  G  L  C  N  G  N  L  V  D  I  F  S  K  V  R  I  F
GCCTCAAGAA GCGGCAGGTTG CGGGCGCCAAG ATCCCCAGCT CAAGGGTATA GTGACCAGGT  300
 G  L  K  K  R  Q  V  R  A  Q  I  P  S  S  R  V  *  V  T  R
TATATTGCAG GCAAGGCTAC TGCACTTGCAAA TGCACCCCGA TGGAGCTCTC GATGGAACCA  360
 L  Y  C  R  Q  G  Y  C  T  C  K  C  T  P  M  E  L  S  D  G  T
AGGATGACAG CACTAATTCT ACACTCTTCA ACCTCATACC AGTGGGACTA CGTGTGTTG  420
 K  D  D  S  T  N  S  T  L  F  N  L  I  P  V  G  L  R  V  V
CCATCCAGGG AGTGAAAACA GGGTTGTATA TAGCCATGAA TGGAGAAGGT TACCTCTACC  480
 A  I  Q  G  V  K  T  G  L  Y  I  A  M  N  G  E  G  Y  L  Y
CATCAGAACT TTTTACCCCT GAATGCAAGT TTAAAGAAAT CGTTTTTGAA AATTATTATG  540
 A  Q  E  L  F  T  P  E  C  K  F  K  E  S  V  F  E  N  Y  Y
TAAATCTACT ATCCATGTTG TACAGACAAC AGGAATCTGG TAGAGCCTGG TTTTTGGGAT  600
 V  I  Y  S  M  L  Y  R  Q  Q  E  S  G  R  A  W  F  L  G
TAAATAAGGA AGGGCAAGCT TACAAAGGGA ACAGAGTAAA GAAAACCAAA CCAGCAGCTC  660
 L  N  K  E  G  Q  A  Y  K  G  N  R  V  K  K  T  K  P  A  A
ATTTTCTACC CAAGCCATTG GAAGTTGCCA TGTACCGAGA ACCATCTTG CATGATGRTTG  720
 H  F  L  P  K  P  L  E  V  A  M  Y  R  E  P  S  L  H  D  V
GGGAAACGGT CCCGAAGCCT GGGGTGACGC CAAGTAAAAG CACAAGTGCG TCTGCAATAA  780
 G  E  T  V  P  K  P  G  V  T  P  S  K  S  T  S  A  I  *
TGAATGGAGG CAAACCAGTC AACAAGAGTA AGACAACATA GCCAGATCCT CACAGGTGTT  840
 M  N  G  G  K  P  V  N  K  S  K  T  T
```

FIG. 8B

SEQ ID NO:4
GTGACTTATT CGTCCTGAGC ACAGTTGAGT GATTTATCCT CACCAGACAT TCCTGCTCCG 900
TGGCTGAAGA GCAGCAGGAA GTAAGCTAAT GCTTATTCTT TGCTGTCTCC GAACTTCTCT 960
GTTGCAAGTG G

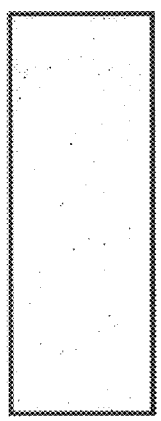 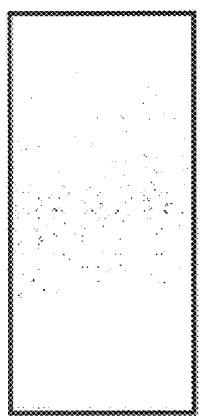 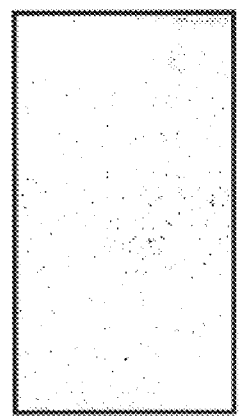 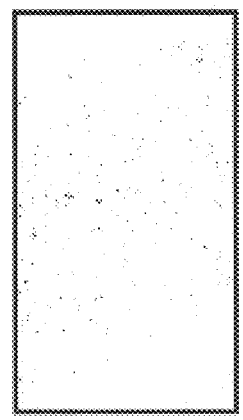 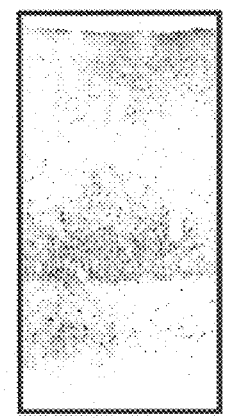
*FIG. 12A*   *FIG. 12B*   *FIG. 12C*   *FIG. 12D*   *FIG. 12E*
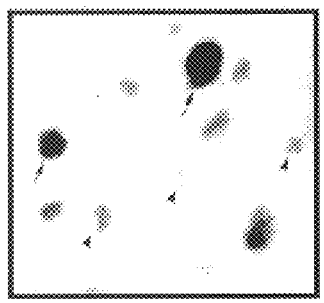 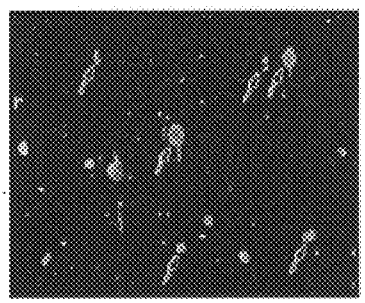 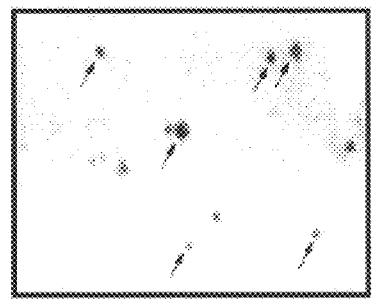
*FIG. 12F*   *FIG. 12G*   *FIG. 12H*
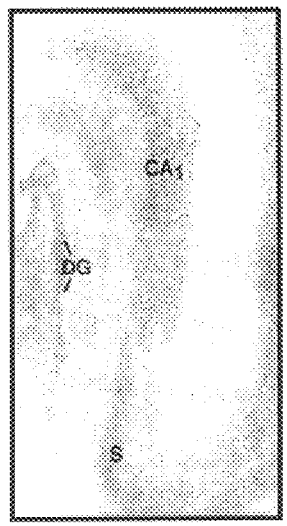 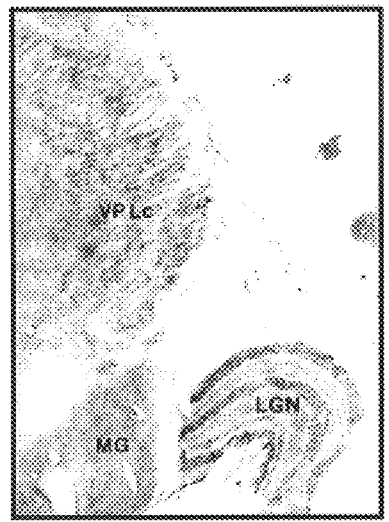 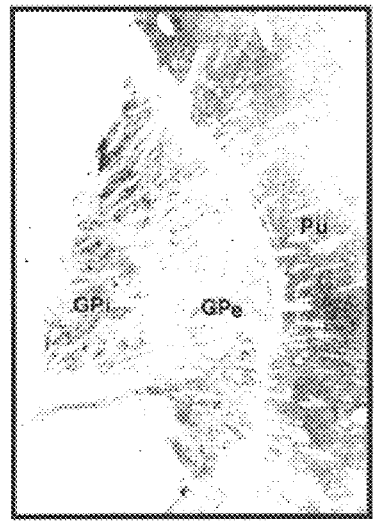
*FIG. 12I*   *FIG. 12J*   *FIG. 12K*

FIBROBLAST GROWTH FACTOR HOMOLOGOUS FACTORS (FHFS) AND METHODS OF USE

BACKGROUND OF THE INVENTION

1. Field of the Invention

The invention relates generally to polypeptide growth factors and specifically to fibroblast growth factor homologous factors (FHFs) and nucleic acids encoding FHFs.

2. Description of Related Art

The fibroblast growth factor (FGF) family encompasses a group of structurally related proteins with a wide range of growth promoting, survival, and differentiation activities in vivo and in vitro (reviewed in Baird and Gospodarowicz, N.Y. Acad. Sci., 638:1, 1991; Eckenstein, J. Neurobiology, 25:1467, 1994; Mason, Cell, 78:547, 1994). As of June, 1996, nine members of this family had been characterized by molecular cloning and their sequences published. The first two members of the family to be characterized, acidic FGF (aFGF/FGF-1) and basic FGF (bFGF/FGF-2), have been found in numerous tissues, including brain, eye, kidney, placenta, and adrenal tissues (Jaye, et al., Science, 233:541, 1986; Abraham, et al., Science, 233:545, 1986). These factors have been shown to be potent mitogens and survival factors for a variety of mesoderm and neuroectoderm-derived tissues, including fibroblasts, endothelial cells, hippocampal and cerebral cortical neurons, and astroglia (Burgess and Maciag, Ann. Rev. Biochemistry, 58:575, 1989). Another member of the FGF family is int-2/FGF-3, which is encoded by a gene that is a common target for activation by the mouse mammary tumor virus, and therefore is presumed to be an oncogenic factor (Smith, et al., EMBO J., 7:1013, 1988). The genes encoding FGF-4, FGF-5, and FGF-6 have transforming activity when introduced into NIH 3T3 cells (Delli-Bovi, et al., Cell, 50:729, 1987; Zhan, et al., Mol. Cell. Biol., 8:3487, 1988; Marics, et al., Oncogene, 4:335, 1989), while keratinocyte growth factor (KGF)/FGF-7, FGF-8, and FGF-9 are mitogenic for keratinocytes, mammary carcinoma cells, and astrocytes, respectively (Finch, et al., Science, 245:752, 1989; Tanaka, et al., Proc. Natl. Acad. Sci. USA, 89:8928, 1992; Miyamoto, et al., Mol. Cell Biol., 13:4251, 1993). Recent experiments indicate that several FGFs have bioactivities that were not evident during their initial identification. For example, FGF-2 has been shown to induce ventral mesoderm in Xenopus embryos (Slack, et al., Nature 326:197–200, 1987; Kimmelman, et al., Cell 51:869–877, 1989), FGF-4 has been shown to be involved in growth and patterning of the chick limb bud (Niswander, et al., Nature 371:609–612, 1994), FGF-5 has been shown to control hair follicle cycling in the mouse (Hebert, Cell 78:1017–1025, 1994), and FGF-8 has been shown to cause duplications of the embryonic chick midbrain (Crossley, et al., Nature 380:66–68, 1996). Several of the FGFs, including aFGF (FGF-1) and bFGF (FGF-2), lack classical signal sequences, and the mechanism by which they are secreted is not known. Current data indicate that FGF-1 and FGF-2 are released from cells by a route that is distinct from the ER-Golgi secretory pathway (Florkiewicz, et al., J. Cell Physiol. 162:388–399, 1995; Jackson, et al, J. Biol. Chem. 270:33–36, 1995).

The nine published members of the FGF family, FGFs 1–9, are between 155 and 268 amino acids in length and share approximately 25% or more amino acid sequence identity, as well as a conserved central region of approximately 140 amino acids. This region forms a compact beta-barrel with three-fold symmetry that is nearly identical in structure to the folded core of interleukins 1-alpha and 1-beta (Zhu, et al., Science 251:90–93, 1991; Zhang, et al., Proc. Natl. Acad. Sci. USA 88:3446–3450,1991; Eriksson, et al., Proc. Natl. Acad. Sci. USA 88:3441–3445, 1991; Ago, et al., J. Biochem. 110:360–363, 1991). FGF-1 and FGF-2 also resemble interleukin 1-beta in lacking a classical signal sequence.

FGF signaling is generally thought to occur by activation of transmembrane tyrosine kinase receptors. For example, FGF-1, FGF-2, and FGF-7/KGF have been shown to exert some or all of their biological activities through high affinity binding to such receptors (see, e.g., Lee, et al., Science, 245:57, 1989; reviewed in Johnson and Williams, Adv. Cancer Res., 60:1, 1993). Four FGF receptor (FGFR) genes have been identified thus far (Johnson, et al., Adv. Cancer Res. 60:1–41, 1993), and activating or inactivating receptor mutations have been described for a subset of these genes, in both mice and humans. In the mouse, disruption of the FGFR1 or FGFR2 genes leads to early embryonic lethality (Deng, et al., Genes Dev. 8:3045–3057,1994; Yamaguchi, et al., Genes Dev. 8:3032–3044, 1994), and disruption of FGFR3 leads to bone overgrowth (Deng, et al., Cell 84:911–921, 1996; Colvin, et al., Nature Genet. 12:390–397, 1996). In humans, point mutations in FGFR1, FGFR2, and FGFR3 have been found in a variety of skeletal disorders (reviewed by Muenke and Schell, Trends Genet. 11, 308–313, 1995). Recent work has shown that receptor diversity is increased by alternative pre-mRNA splicing within the extracellular ligand binding domain, with the result that multiple receptor isoforms, with different ligand binding properties, can be encoded by the same gene (Johnson and Williams, supra). In tissue culture systems, binding of aFGF or bFGF to its cell surface receptor activates phospholipase C-gamma (Burgess, et al., Mol. Cell Biol., 10:4770, 1990), which is a component of a pathway known to integrate a variety of mitogenic signals. Many members of the FGF family also bind tightly to heparin, and a ternary complex of heparin, FGF, and a transmembrane receptor may be a biologically relevant signaling species.

SUMMARY OF THE INVENTION

The invention provides fibroblast growth factor homologous factor (FHF) polypeptides and nucleic acids that encode them. FHFs are involved in regulating the growth, survival, and differentiation of cells in the central nervous system (CNS), as well as cells in peripheral nervous tissues.

The invention also provides methods for detecting alterations in FHF gene expression, which can be used in the diagnosis of neurodegenerative and neoplastic disorders. Methods for treating neurodegenerative and neoplastic disorders, in which the expression and/or activity of an FHF is modulated, are also included in the invention.

BRIEF DESCRIPTION OF THE DRAWINGS

FIG. 1 shows an alignment o the amino acid sequences of FHF-1 (SEQ ID NO:1), FHF-2 (SEQ ID NO:2), FHF-3 (SEQ ID NO:3), and FHF-4 (SEQ ID NO:4). Amino acids that are conserved in all four of FHFs 1–4 are shaded and boxed and amino acids that are conserved in only some of FHFs 1–4 are shaded.

FIGS. 2A–2B show an alignment of the amino acid sequences of FHF-1 (SEQ ID NO:1), FHF-2 (SEQ ID NO:2), FHF-3 (SEQ ID NO:3), FHF-4 (SEQ ID NO:4), FGF-1 (SEQ ID NO:5), FGF-2 (SEQ ID NO:6), and FGF-9 (SEQ ID NO:7). The large, black dots indicate amino acids that are identical among FHFs 1–4, but that are different in the nine previously characterized FGFs (FGFs 1–9). Intron locations for murine FHF-2 are indicated by arrowheads above the aligned sequences. The locations of the twelve segments having beta-sheet conformations in the FGF-2 crystal structure are underlined (Erickson, et al., *Proc. Natl. Acad. Sci. USA* 88:3441–3445, 1991).

FIGS. 3A–3E show an alignment of the amino acid sequences of mouse and human FHFs with each of the nine, previously characterized members of the FGF family (hFHF-1 (SEQ ID NO:1), hFHF-2 (SEQ ID NO:2), hFHF-3 (SEQ ID NO:3), hFHF-4 (SEQ ID NO:4), mFHF-1 (SEQ ID NO:8), mFHF-2 (SEQ ID NO:9), mFHF-3 (SEQ ID NO:10), and mFHF-4 (SEQ ID NO:11)).

The FGF family members include aFGF/FGF-1 (SEQ ID NO:5; Jaye, et al., supra), bFGF/FGF-2 (SEQ ID NO:6; Abraham, et al., supra), int-2/FGF-3 (SEQ ID NO:12; Smith, et al., supra), FGF-4 (SEQ ID NO:13; Delli-Bovi, et al., supra), FGF-5 (SEQ ID NO:14; Zhan, et al., supra), FGF-6 (SEQ ID NO:15; Maricas, et al., supra), keratinocyte growth factor/FGF-7 (SEQ ID NO:16; Finch, et al., supra), FGF-8 (SEQ ID NO:17; Tanaka, et al., supra), and FGF-9 (SEQ ID NO:7; Miyamoto, et al., supra). ("m" denotes mouse, and "h" denotes human.)

Figure 4:
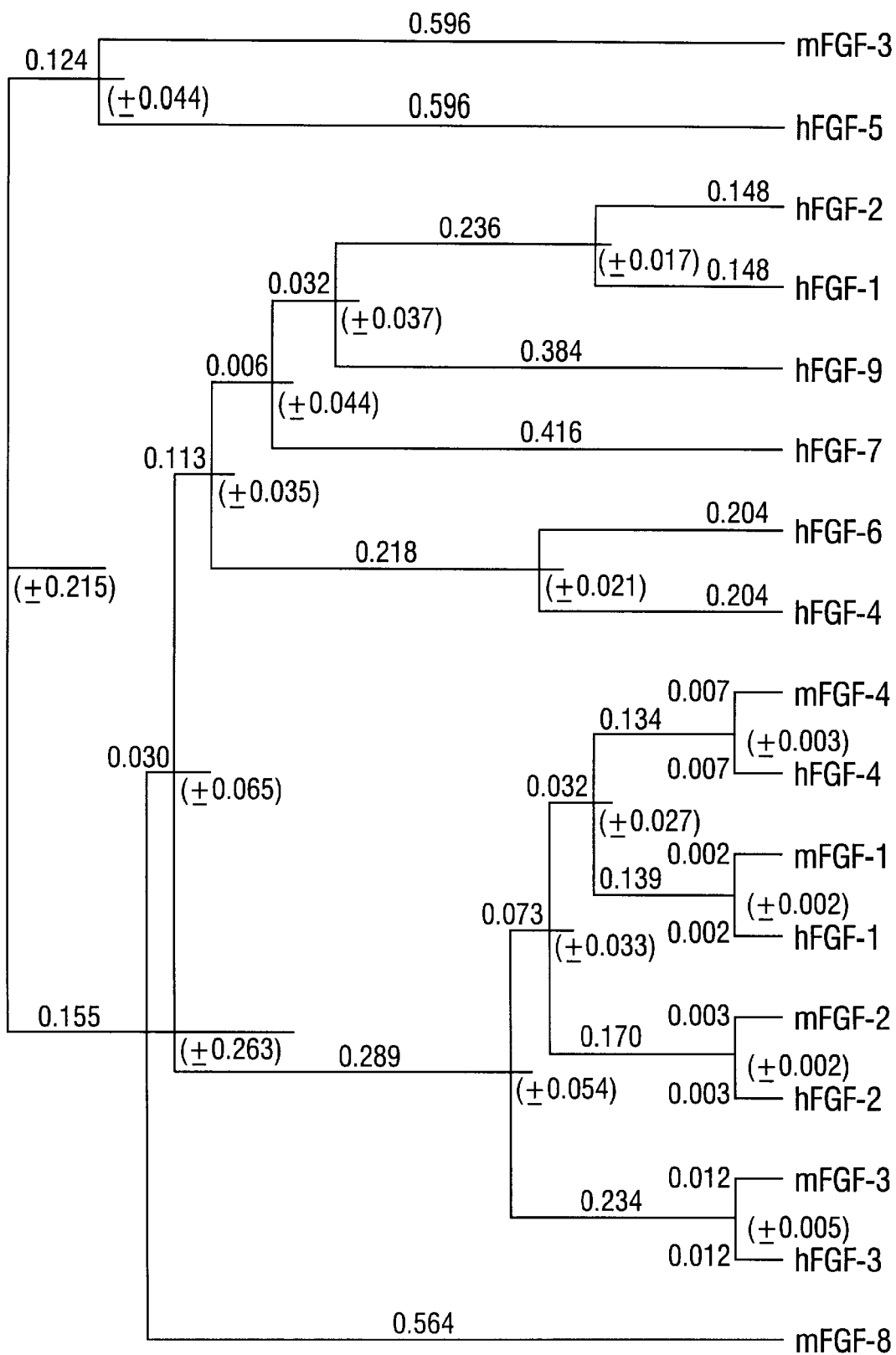

FIG. 4 shows a dendrogram of mammalian FHF and FGF family members, in which the length of each path connecting any pair of FHF or FGF family members is proportional to the degree of amino acid sequence divergence of that pair. ("m" denotes mouse, and "h" denotes human.)

FIGS. 5A–5B show the nucleotide (SEQ ID NO:18) and deduced amino acid (SEQ ID NO:1) sequences of FHF-1.

FIGS. 6A–6B show the nucleotide (SEQ ID NO:19) and deduced amino acid (SEQ ID NO:2) sequences of FHF-2.

FIGS. 7A–7B show the nucleotide (SEQ ID NO:20) and deduced amino acid (SEQ ID NO:3) sequences of FHF-3.

FIGS. 8A–8B show the nucleotide (SEQ ID NO:21) and deduced amino acid (SEQ ID NO:4) sequences of FHF-4.

Figure 9:
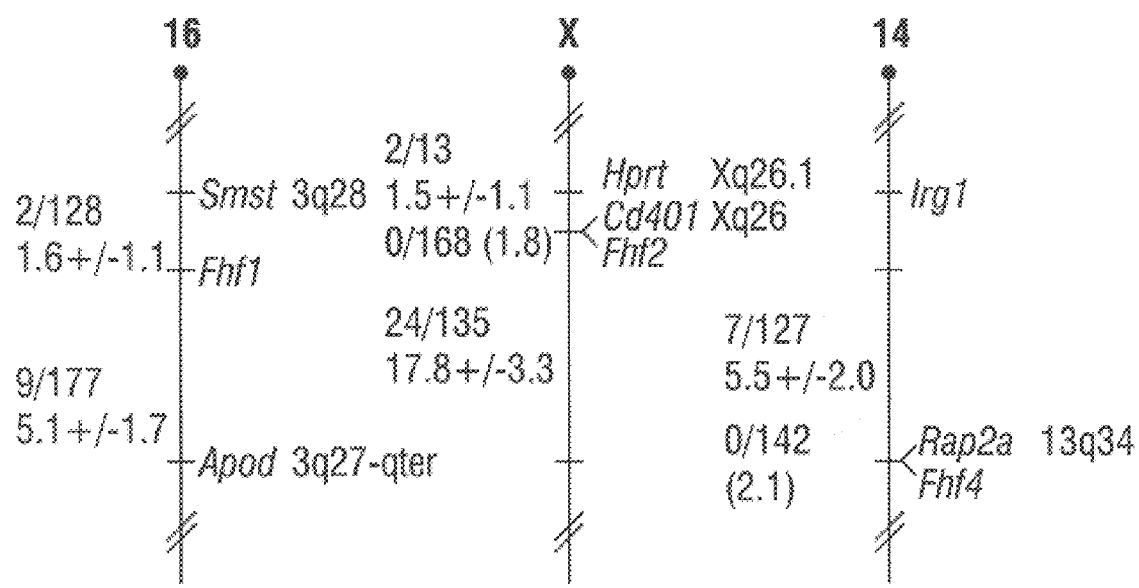

FIG. 9 shows partial chromosome linkage maps for mouse FHF-1, FHF-2, and FHF-3 genes. The genes were mapped by interspecific backcross analysis. To the left of each chromosome map, the number of recombinant N2 animals is presented, divided by the total number of N2 animals typed for each pair of loci. The recombination frequencies, expressed as genetic distance in centimorgans (± one standard error) are also shown. The upper 95% confidence limit of the recombination distance is given in parentheses, in cases where no recombinants were found between loci. The positions of loci on human chromosomes, where known, are shown to the right of the chromosome maps. References for the map positions of most human loci can be obtained from the GDB (Genome Data Base), which is a computerized database of human linkage information maintained by The William H. Welch Medical Library of The Johns Hopkins University (Baltimore, Md.).

Figure 10:
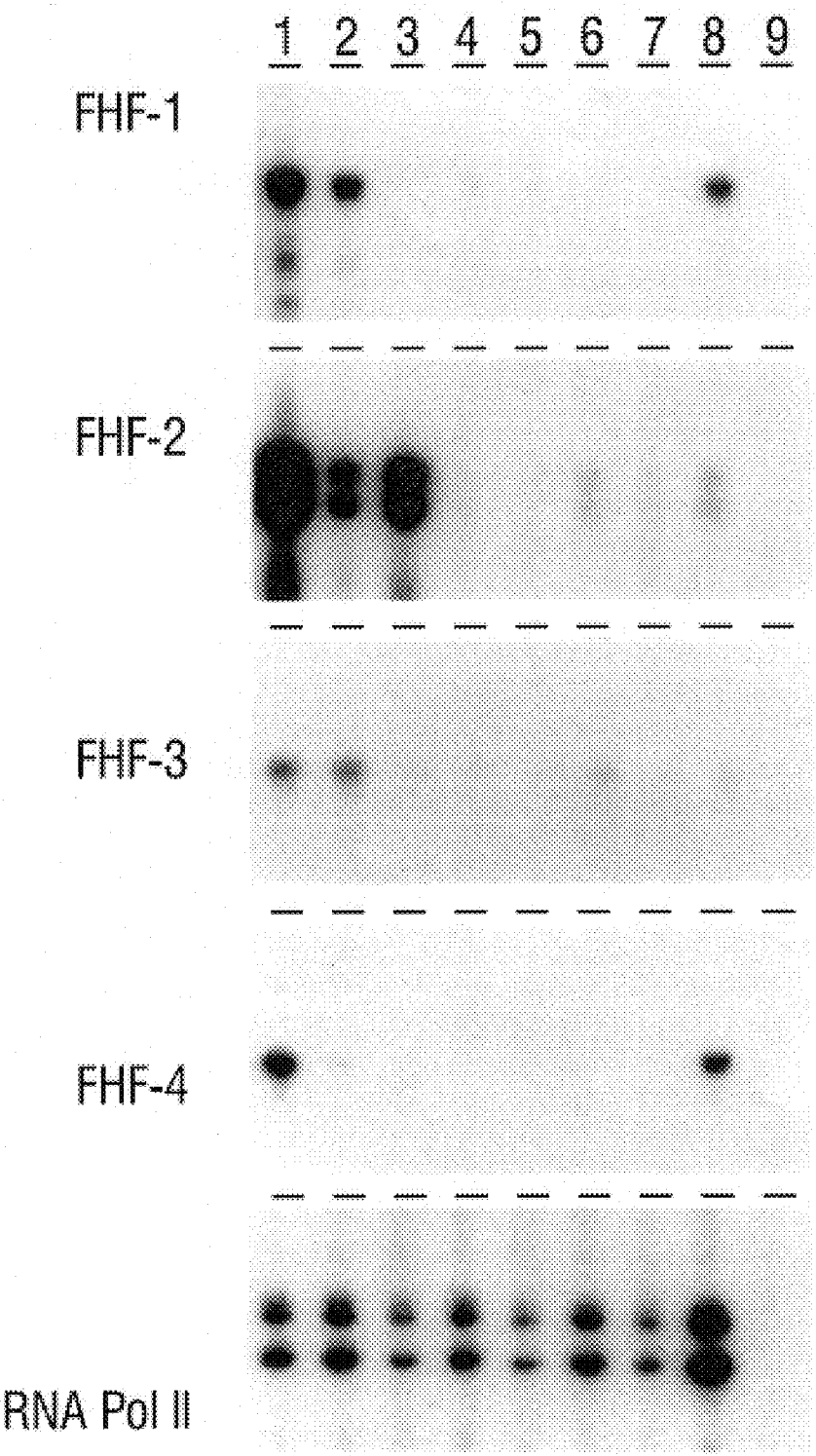

FIG. 10 shows the tissue distribution of FHF transcripts in the adult mouse. Ten micrograms of total RNA from various mouse tissues was prepared (Chomczinski and Sacchi, *Anal. Biochem.*, 162:156, 1987) and used in RNAse protection experiments (Ausubel, et al., *Current Protocols in Molecular Biology*, Wiley Interscience, New York, N.Y., 1987) employing the indicated antisense riboprobes (FHFs 1–4). The RNA samples are as follows: 1, brain; 2, eye; 3, heart; 4, kidney; 5, liver; 6, lung; 7, spleen; 8, testis; and 9, yeast tRNA. A control reaction, in which an RNA Polymerase II probe was used, is shown at the bottom of the figure.

FIGS. 11A–L show in situ localization of FHF transcripts in sections prepared from the developing and adult mouse.

$^{33}$P in situ hybridization is shown in red and is superimposed on a cresyl violet stain shown in black and white. The probes and samples used are as follows: (A) FHF-2, e11; (B) FHF-3, e11; (C, D) FHF-2, e17; (E) FHF-1, P1, coronal section through the head at the level of the eyes; (F) FHF-2, P1, coronal section through the center of the head; (G) FHF-1, adult; (H, I) FHF-2, adult; (J) FHF-3, adult; (K, L) FHF-4, adult.

FIGS. 12A–K show FHF-1 immunostaining in sections of the macaque monkey CNS. The samples stained are as follows: (A) precentral motor cortex; (B) area 3b in the primary somatosensory cortex; (C) primary auditory cortex; (D) area 7b in the superior parietal lobule; and (E) primary visual cortex. Panels F–H show that populations of cortical neurons immunoreactive for FHF-1 include large intensely, immunoreactive cells (arrows), small, weakly immunoreactive cells (arrowheads), and small, weakly immunoreactive cells, with fine processes resembling microglia (double arrows). Simultaneous immunostaining for parvalbumin (G) and FHF-1 (H) shows that large and small neurons are immunoreactive for both. An uneven distribution of FHF-1 immunoreactive somata is seen in the hippocampal formation (I), including the subicular complex (S), the CA fields, and the dentate gyrus (DG). In the dorsal thalamus (J), FHF-1 immunoreactive somata occupy patches in the caudal ventroposteriolateral nucleus (VPLc) and are found in both magnocellular and parvicellular layers of the lateral geniculate nucleus (LGN). The medial geniculate complex contains few immunostained cells. In the basal telencephalon (K), immunoreactive neurons are present in both the external and internal segments of the globus pallidus (Gpe and GPi). Scale bars: 500 μm in (A–E), 20 μm in (F), 75 μm in (G, H), and 1 mm in (I–K).

Figure 13:
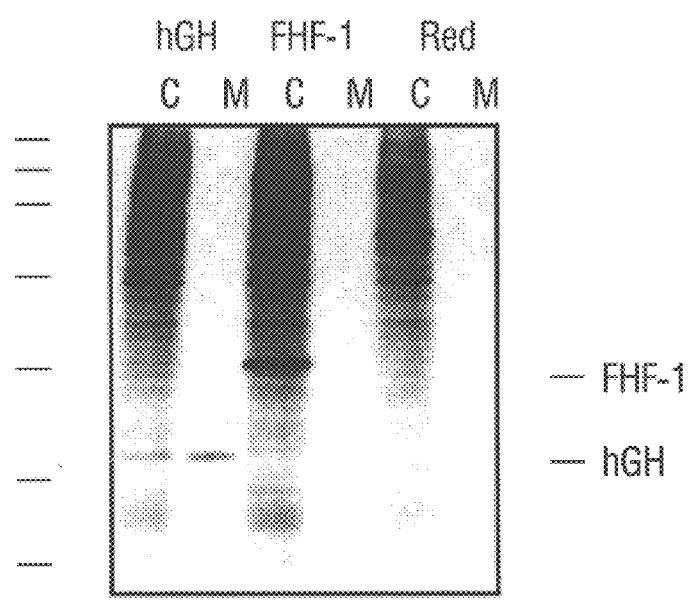

FIG. 13 shows that FHF-1 is not secreted by 293 cells, which are human embryonic kidney cells. 293 cells were transiently transfected with plasmids directing expression of human growth hormone (left 2 lanes; hGH), FHF-1 (center 2 lanes), or the human red cone pigment (right 2 lanes; Red). The cells were labeled for 6 hours with $^{35}$S-methionine in serum-free medium, and the total protein present in the cells (C) or medium (M) was resolved by SDS-PAGE and visualized by autoradiography. Secretion of hGH, but not FHF-1, is observed. The mobilities of protein standards are indicated at the left of the figure; from top to bottom, their molecular masses, in kDa, are: 220, 97, 66, 46, 30, 21.5, and 14.3. The mobilities of hGH and FHF-1 are indicated at the right side of the figure.

Figure 14:
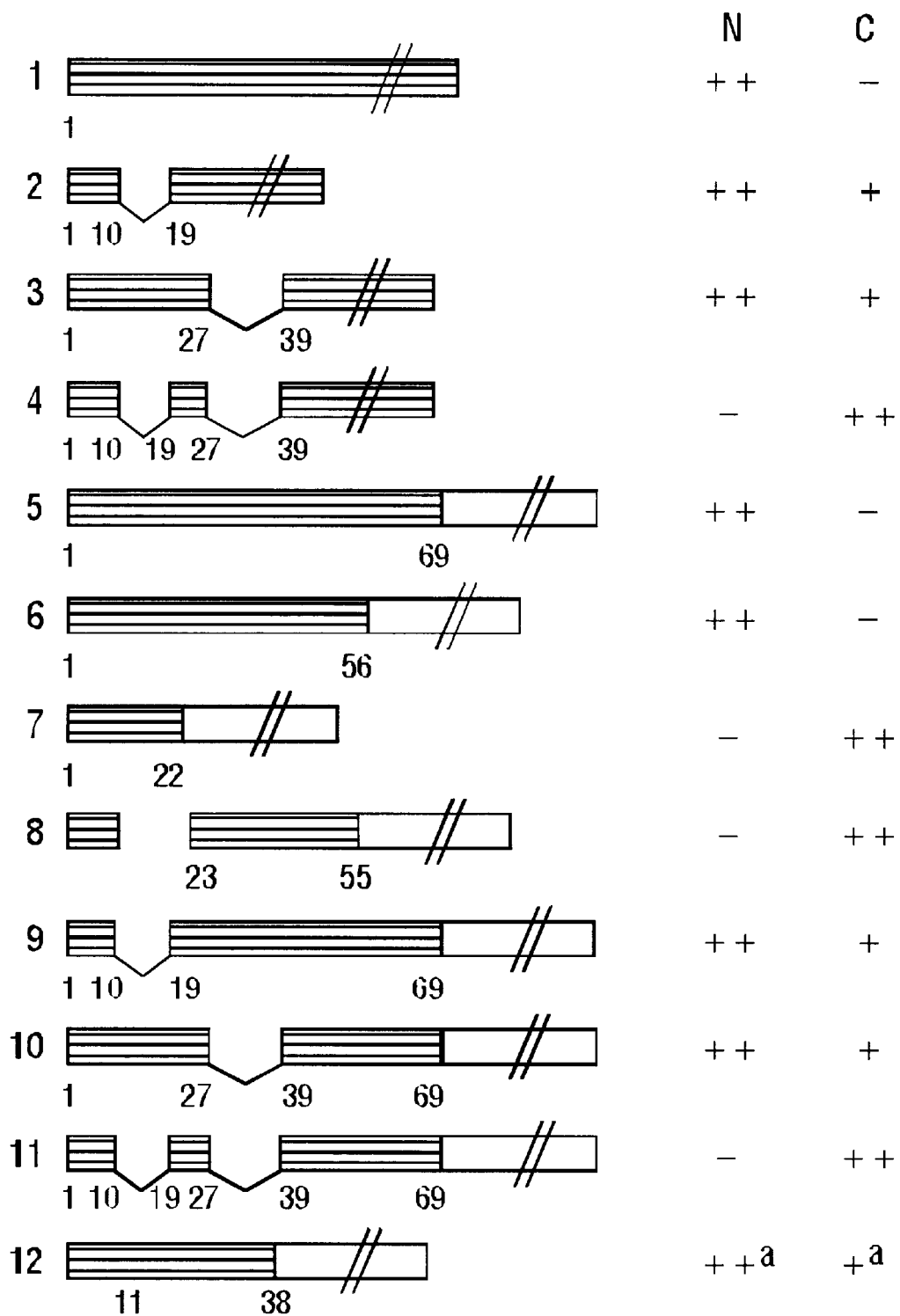
Figure 15A:
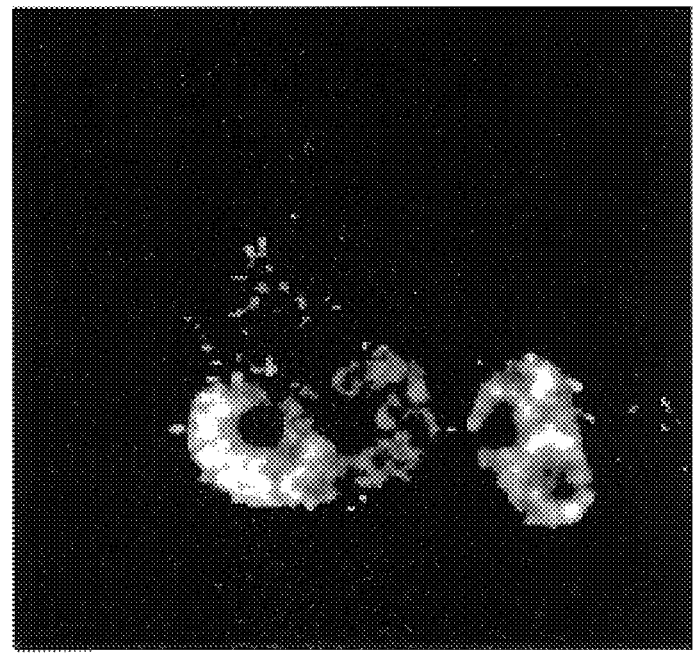
Figure 15B:
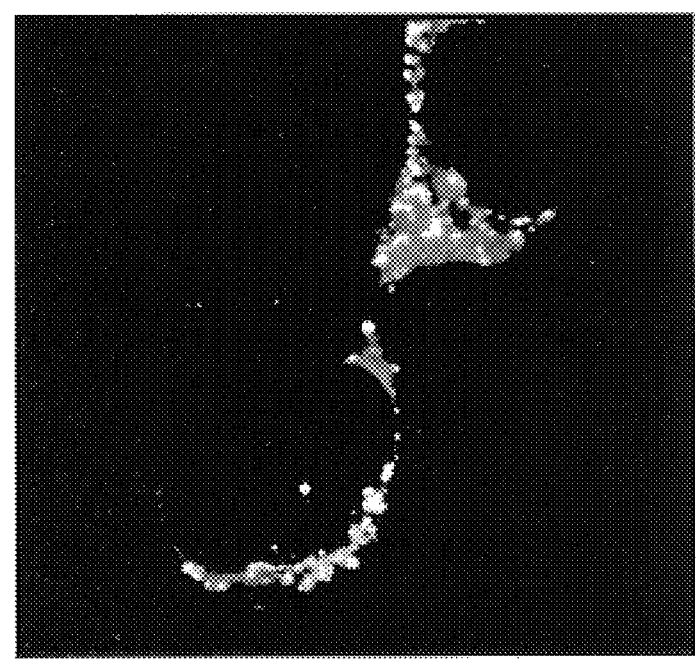
Figure 15C:
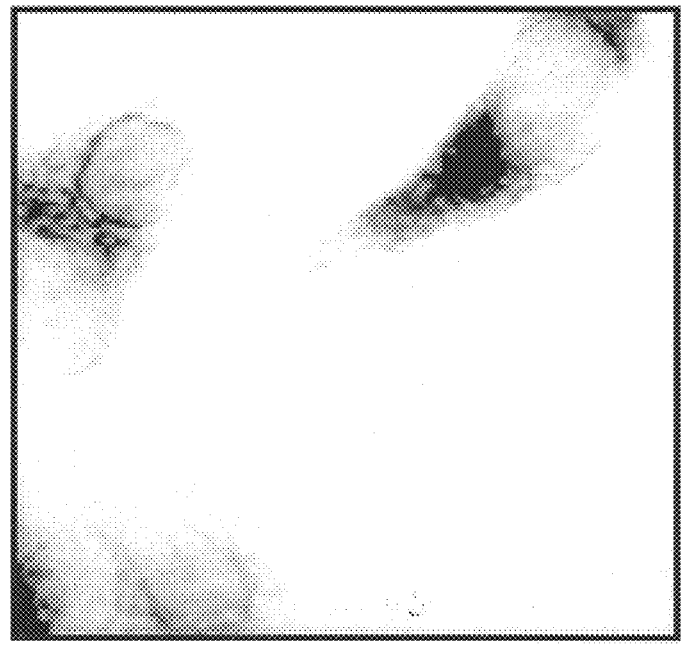
Figure 15D:
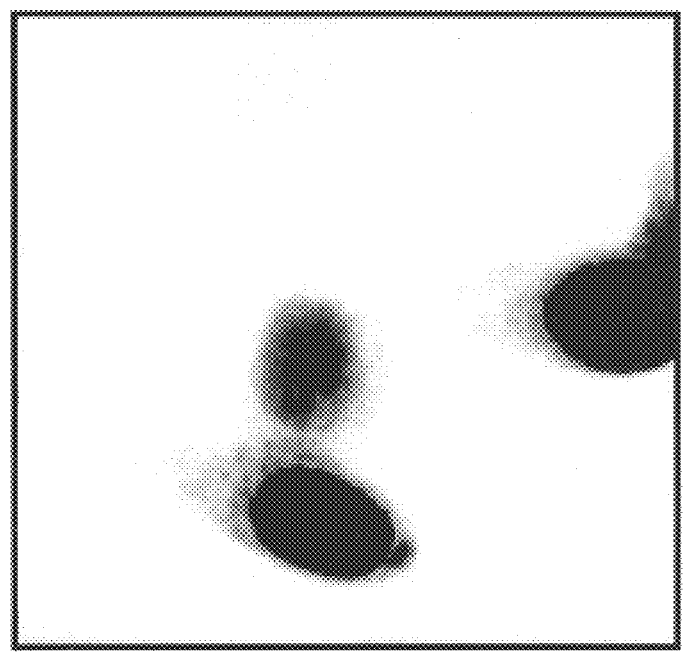
Figure 15E:
Figure 15F:
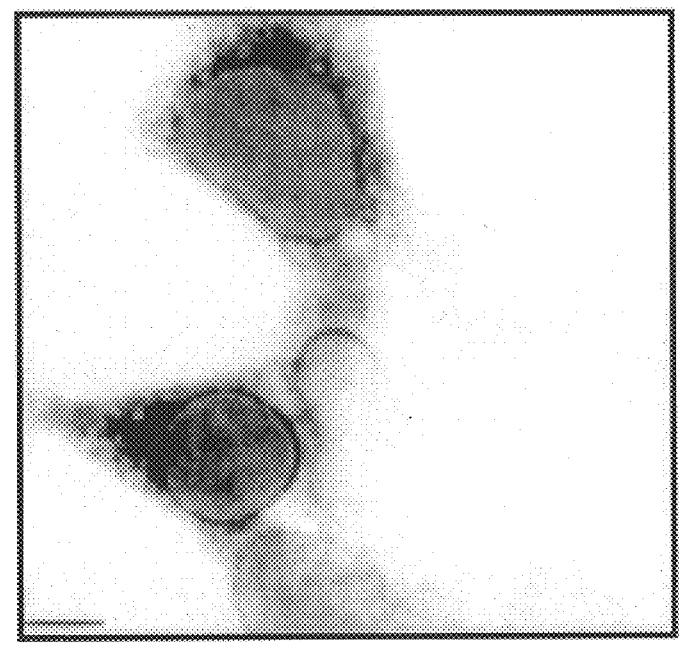

FIG. 14 shows a summary of FHF-1 constructs used to identify the FHF-1 nuclear localization signal (NLS). Localization of these constructs by immunostaining (constructs 1–4) and localization of FHF-1-β-galactosidase fusions by X-gal staining (constructs 5–12) is also shown. The numbers underneath each construct indicate the amino acids from FHF-1 that are present in the construct. (N, nuclear staining; C, cytoplasmic staining; ++, strong staining; +, weak staining; –, no staining. 'a', construct 12 shows cytoplasmic staining in 15%–20% of cells and nuclear localization in 80%–85% of cells.)

FIGS. 15A–F show double label immunofluorescent localization of the constructs illustrated in FIG. 14. The antibodies used are as follows: (A, B) double label immunofluorescent localization of FHF-1 (green) and BiP (an ER marker; red), optically sectioned at 0.7 μm; and (C–F) histochemical localization of FHF-1-β-galactosidase fusion proteins. All experiments were performed in transiently transfected 293 cells. The constructs used are: (A) full length FHF-1, construct 1; (B) construct 4; (C) fill length β-galactosidase; (D) construct 6; (E) construct 11; (F) construct 12.

DETAILED DESCRIPTION OF THE INVENTION

The invention provides polypeptide growth factors, designated fibroblast growth factor homologous factors (FHFs), and nucleic acids that encode them. Genes encoding four FHFs, designated FHFs 1–4, have been isolated and sequenced. The deduced amino acid sequence of FHF-1 is 27% identical to that of FGF-9, and the amino acid sequences of FHFs 1–4 are 58–70% identical to each other. Thus, FHFs define a new branch of the FGF family.

FHFs are expressed in the developing and adult nervous systems, and thus are believed to play roles in regulating nervous system development and function. Accordingly, FHF polypeptides, and nucleic acids that encode them, can be used in methods for treating and diagnosing conditions affecting the nervous system, including, e.g., stroke, neurodegenerative diseases, such as Parkinson's disease and Alzheimer's disease, retinal degenerative diseases, such as retinitis pigmentosa and macular degeneration, cerebellar degenerative diseases, and cancer. More specific uses for FHF-related molecules can be gleaned from their tissue specificities. For example, although FHFs 1–4 are all expressed in the brain, FHFs 1–3 are specifically expressed in the eye, FHFs 1 and 4 are expressed in the testes, and FHF-2 is expressed in the heart. Thus, monoclonal and polyclonal antibodies can be produced using standard immunization and screening methods well known in the art. These antibodies can be easily detectably labelled and used histologically to identify tissues which contain a given FHF. FHFs can also be used in methods for maintaining cultured cells or tissues, such as neuronal cells or tissues, prior to transplantation. In addition, FHFs can be used to promote neuron growth in vitro, in order to, for example, facilitate production of growth factors, such as interleukin-2 (IL-2), that are produced by them. Methods employing FHF polypeptides and nucleic acids are described in further detail below.

The invention provides substantially pure FHF polypeptides. FHF polypeptides can be characterized as containing, for example, at least five consecutive amino acids that are conserved in at least two, e.g., three or four, FHFs, such as FHFs 1–4. One or more (e.g., two to four) of the five conserved amino acids, in addition to being conserved in FHFs, can be characterized as not being conserved in any of the nine previously characterized FGFs (FGFs 1–9, see above).

The term "substantially pure" is used herein to describe a molecule, such as a polypeptide (e.g., an FHF polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify FHF polypeptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

FHF polypeptides included in the invention can have one of the amino acid sequences of FHFs 1–4, for example, the amino acid sequence of FHF-4. FHF polypeptides, such as FHFs 1–4, can be characterized by being expressed in the brain, lacking classical signal sequences, containing nuclear localization signals or nuclear localization-like signals, and containing, at full length, about 225–250 amino acids (FHF-1:244 amino acids; FHF-2:245 amino acids; FHF-3:225 amino acids; FHF-4:247 amino acids; see, e.g., FIGS. 1–3 and 5–8). The FHF polypeptides of the invention can be derived from a mammal, such as a human or a mouse.

Also included in the invention are polypeptides having sequences that are "substantially identical" to the sequence of an FHF polypeptide, such as one of FHFs 1–4, e.g., FHF-4. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitutions, deletions, or insertions, provided that the polypeptide retains at least one FHF-specific activity or an FHF-specific epitope. For example, one or more amino acids can be deleted from an FHF polypeptide, resulting in modification of the structure of the polypeptide, without significantly altering its biological activity. For example, amino- or carboxyl-terminal amino acids that are not required for FHF biological activity, can be removed. Such modifications can result in the development of smaller active FHF polypeptides.

Other FHF polypeptides included in the invention are polypeptides having amino acid sequences that are at least 50% identical to the amino acid sequence of an FHF polypeptide, such as any of FHFs 1–4, e.g., FHF-4. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra).

The invention also includes fragments of FHF polypeptides, such as FHFs 1–4, that retain at least one FHF-specific activity or epitope. For example, an FHF polypeptide fragment containing, e.g., at least 8–10 amino acids can be used as an immunogen in the production of FHF-specific antibodies. The fragment can contain, for example, an amino acid sequence that is conserved in FHFs, and this amino acid sequence can contain amino acids that are conserved in FHFs, but not in FGFs 1–9. Such fragments can easily be identified by comparing the sequences of FHFs and FGFs, e.g., by reference to FIGS. 1–3. In addition to their use as peptide immunogens, the above-described FHF fragments can be used in immunoassays, such as ELISAs, to detect the presence of FHF-specific antibodies in samples.

The FHF polypeptides of the invention can be obtained using any of several standard methods. For example, FHF polypeptides can be produced in a standard recombinant expression systems (see below), chemically synthesized (this approach may be limited to small FHF peptide fragments), or purified from tissues in which they are naturally expressed (see, e.g., Ausubel, et al., supra).

The invention also provides isolated nucleic acid molecules that encode the FHF polypeptides described above, as well as fragments thereof For example, nucleic acids that encode any of FHFs 1–4, such as FHF-4, are included in the invention. These nucleic acids can contain naturally occurring nucleotide sequences (see FIGS. 1–3 and 5–8), or sequences that differ from those of the naturally occurring nucleic acids that encode FHFs 1–4, but encode the same amino acids, due to the degeneracy of the genetic code. The nucleic acids of the invention can contain DNA or RNA nucleotides, or combinations or modifications thereof.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of FHF gene products (e.g., FHF RNAs and FHF polypeptides; see below). In addition, the nucleic acid molecules that encode FHF polypeptides (and fragments thereof) and related nucleic acids, such as (1) nucleic acids containing sequences that are complementary to, or that hybridize to, nucleic acids encoding FHF polypeptides, or fragments thereof (e.g., fragments containing at least 12, 15, 20, or 25 nucleotides); and (2) nucleic acids containing sequences that hybridize to sequences that are complementary to nucleic acids encoding FHF polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing FHF nucleic acids, methods for detecting the presence of an FHF nucleic acid in a sample, screening methods for identifying nucleic acids encoding new FHF family members, and therapeutic methods.

The invention also includes methods for identifying nucleic acid molecules that encode members of the FHF polypeptide family in addition to FHFs 1–4. In these methods, a sample, e.g., a nucleic acid library, such as a cDNA library, that contains a nucleic acid encoding an FHF polypeptide is screened with an FHF-specific probe, e.g., an FHF-specific nucleic acid probe. FHF-specific nucleic acid probes are nucleic acid molecules (e.g., molecules containing DNA or RNA nucleotides, or combinations or modifications thereof) that specifically hybridize to nucleic acids encoding FHF polypeptides, or to complementary sequences thereof. Because FHFs are closely related to FGFs (i.e., the first nine members of the FGF family (FGFs 1–9), see above), the term "FHF-specific probe," in the context of this method of invention, refers to probes that bind to nucleic acids encoding FHF polypeptides, or to complementary sequences thereof, to a detectably greater extent than to nucleic acids encoding FGFs, or to complementary sequences thereof. The term "FHF-specific probe" thus includes probes that can bind to nucleic acids encoding FHF polypeptides (or to complementary sequences thereof), but not to nucleic acids encoding FGFs (or to complementary sequences thereof), to an appreciable extent.

The invention facilitates production of FHF-specific nucleic acid probes. Methods for obtaining such probes can be designed based on the amino acid sequence alignments shown in FIGS. 1–3. In FIG. 1, for example, amino acid sequences that are conserved in FHFs ("FHF-conserved amino acids") are boxed. In FIG. 2, amino acids that are conserved in FHFs, but not in FGFs (i.e., FGFs 1–9) ("FHF-specific amino acids"), are indicated by large, black dots. The probes, which can contain at least 12, e.g., at least 15, 25, 35, 50, 100, or 150 nucleotides, can be produced using any of several standard methods (see, e.g., Ausubel, et al., supra). For example, preferably, the probes are generated using PCR amplification methods, such as those described below in Example 1. In these methods, primers are designed that correspond to FHF-conserved sequences (FIG. 1), which can include FHF-specific amino acids, and the resulting PCR product is used as a probe to screen a nucleic acid library, such as a cDNA library. A nucleotide sequence encoding FHF-4 was identified generally following this process based upon the analysis of the sequences of FHF 1–3.

As is known in the art, PCR primers are typically designed to contain at least 15 nucleotides, for example 15–30 nucleotides. The design of FHF-specific primers containing 21 nucleotides, which encode FHF peptides containing 7 amino acids, are described as follows. Preferably, most or all of the nucleotides in such a probe encode FHF-conserved amino acids, including FHF-specific amino acids. For example, primers containing sequences encoding peptides containing at least 40% FHF-conserved amino acids can be used. Such a primer, containing 21 nucleotides, can include sequences encoding at least 3/7, 4/7, 5/7, 6/7, or 7/7 FHF-conserved amino acids. As can be determined by analysis of FIGS. 1–3, in the case of a 21 nucleotide primer, encoding 7 amino acids, up to 5 amino acids can be FHF-specific. Thus, the primer can contain sequences encoding at least one FHF-specific amino acid, for example, up to 5 FHF-specific amino acids. Once FHF-specific amino acid sequences are selected as templates against which primer sequences are to be designed, the primers can be synthesized using, e.g., standard chemical methods. As is described above, due to the degeneracy of the genetic code, such primers should be designed to include appropriate degenerate sequences, as can readily be determined by one skilled in the art (see above, and Example 1, below).

Based on the guidelines presented above, examples of FHF-conserved amino acid peptides that can be used as templates for the design of FHF-specific primers are as follows. Additional examples can be found by analysis of sequence alignments of FHF polypeptides, for example, the alignments in FIGS. 1–3. Primers can be designed, for example, based on 5–10 amino acid regions of these peptides, depending on the lengths of the primers desired. For example, primers can be designed to correspond to 7 consecutive amino acids of any of the segments shown below.

1. AAAI/LASS/GSLIRQKR(SEQ ID NO:22) (corresponding to amino acids 2–14 of human FHF-1)
2. PQLKGIVTR/K(SEQ ID NO:23) (corresponding to amino acids 68–76 of human FHF-1)
3. TL/HFNLIPVGLRVV(SEQ ID NO:24) (corresponding to amino acids 104–116 of human FHF-1)
4. AMNG/S/AEGY/LLY(SEQ ID NO:25) (corresponding to amino acids 128–136 of human FHF-1)
5. KES/CVFENYYV(SEQ ID NO:26) (corresponding to amino acids 148–157 of human FHF-1; see Example 1, below, for an example of a primer based on the "VFENYYV" (SEQ ID NO:27) portion of this sequence.)

6. SGRA/GWF/YLGL(SEQ ID NO:28) (corresponding to amino acids 169–177 of human FHF-1)
7. MKGNR/HVKKT/NK(SEQ ID NO:29) (corresponding to amino acids 184–193 of human FHF-1; see Example 1, below, for an example of a primer based on the "MKGNH/RVK" (SEQ ID NO:30) portion of this sequence.)
8. VC/AMYR/Q/KEPSLH(SEQ ID NO:31) (corresponding to amino acids 205–214 of human FHF-1)

As is described above, FHF-specific r\primers, for example primers based on the FHF-specific peptides shown above, or portions thereof, can be used in PCR reactions to generate FHF-specific probes, which can be used in standard screening methods to identify nucleic acids encoding FHF family members (see, e.g., Ausubel, et al., supra).

In addition to FHF-specific nucleic acid probes, FHF-specific polypeptide probes, such as FHF-specific antibodies, can be used to screen samples, e.g., expression libraries, for nucleic acids encoding novel FHF polypeptides, or portions thereof. For example, an antibody that specifically binds to an FHF-specific peptide can be used in this method. Methods for carrying out such screening are well known in the art (see, e.g., Ausubel, et al., supra).

The sequences of a pair of nucleic acid molecules (or two regions within a single nucleic acid molecule) are said to be "complementary" to each other if base pairing interactions can occur between each nucleotide of one of the members of the pair and each nucleotide of the other member of the pair. A pair of nucleic acid molecules (or two regions within a single nucleic acid molecule) are said to "hybridize" to each other if they form a duplex by base pairing interactions between them. As is known in the art, hybridization between nucleic acid pairs does not require complete complementarity between the hybridizing regions, but only that there is a sufficient level of base pairing to maintain the duplex under the hybridization conditions used.

Hybridization reactions are typically carried out under low to moderate stringency conditions, in which specific and some non-specific interactions can occur. After hybridization, washing can be carried out under moderate or high stringency conditions to eliminate non-specific binding. As is known in the art, optimal washing conditions can be determined empirically, e.g., by gradually increasing the stringency. Condition parameters that can be changed to affect stringency include, e.g., temperature and salt concentration. In general, the lower the salt concentration and the higher the temperature, the higher the stringency. For example, washing can be initiated at a low temperature (e.g., room temperature) using a solution containing an equivalent or lower salt concentration as the hybridization solution. Subsequent washing can be carried out using progressively warmer solutions having the same salt solution. Alternatively, the salt concentration can be lowered and the temperature maintained in the washing step, or the salt concentration can be lowered and the temperature increased. Additional parameters can be altered to affect stringency, including, e.g., the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. An example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The nucleic acid molecules of the invention can be obtained by any of several standard methods. For example, the molecules can be produced using standard recombinant, enzymatic (e.g., PCR or reverse transcription (RT)/PCR methods), and chemical (e.g., phosphoramidite-based synthesis) methods. In addition, they can be isolated from samples, such as nucleic acid libraries and tissue samples, using standard hybridization methods. For example, as described above, using standard methods, genomic or cDNA libraries can be hybridized with nucleic acid probes corresponding to FHF nucleic acid sequences to detect the presence of a homologous nucleotide sequence in the library (see, e.g., Ausubel, et al., supra). These methods are described in more detail above. Also as described above, nucleic acids encoding polypeptides containing at least one FHF epitope, such as an FHF-specific epitope, can also be identified by screening a cDNA expression library, such as a library contained in lambda gt11, with an FHF-specific antibody as a probe. Such antibodies can be either polyclonal or monoclonal and are produced using standard methods (see, e.g., Harlow and Lane, *Antibodies: A Laboratory Manual*, Cold Spring Harbor Laboratory Press, Cold Spring Harbor, N.Y., 1988).

The FHF nucleic acid molecules can be inserted into vectors, such as plasmid or viral vectors, that facilitate (1) expression of the inserted nucleic acid molecule and/or (2) amplification of the insert. As is well known in the art, such vectors can contain, e.g., promoter sequences, which facilitate transcription of the inserted nucleic acid in the cell, origins of replication, and genes, such as a neomycin-resistance gene, which encodes a selectable marker that imparts G418 resistance to cells in which it is expressed, and thus permits phenotypic selection of transformed cells.

Vectors suitable for use in the present invention include, e.g., T7-based expression vectors for use in bacteria (see, e.g., Rosenberg, et al., *Gene*, 56:125, 1987), the pMSXND expression vector for use in mammalian cells (Lee and Nathans, *J. Biol. Chem.*, 263:3521, 1988), and baculovirus-derived vectors for use in insect cells. The nucleic acids in such vectors are operably linked to a promoter, which is selected based on, e.g., the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific promoters are available. (See, e.g., Ausubel, et al., supra, for additional appropriate vectors and promoters that can be used in the invention; also see Pouwels, et al., *Cloning Vectors: A Laboratory Manual,* 1985, Supp. 1987). Viral vectors that can be used in the invention include, for example, retroviral, adenoviral, adeno-associated viral, herpes virus, simian virus 40 (SV40), and bovine papilloma virus vectors (see, e.g., Gluzman ed., *Eukaryotic Viral Vectors*, Cold Spring Harbor Laboratory Press, Cold Spring Harbor, N.Y., 1982), and are discussed further below.

Cells into which FHF nucleic acids can be introduced, in order to, for example, produce FHF polypeptides using, e.g., the vectors described above, include prokaryotic cells (e.g., bacterial cells, such as *E. coli* cells) and eukaryotic cells (e.g., yeast cells, such as *Saccharomyces cerevisiae* cells; insect cells, such as *Spodoptera frugiperda* cells (e.g., Sf-9 cells); and mammalian cells, such as CHO, Cos-1, NIH-3T3, and JEG3 cells). Such cells are available from a number of different sources that are known to those skilled in the art, e.g., the American Type Culture Collection (ATCC), Rockville, Md. (also see Ausubel, et al., supra). Cells into which the nucleic acids of the invention have been introduced, as well as their progeny, even if not identical to the parental cells, due to mutations, are included in the invention.

Methods for introducing the nucleic acids of the invention (e.g., nucleic acids inserted into the vectors described above) into cells, either transiently or stably, are well known in the art (see, e.g., Ausubel, et al., supra). For example, in the case of prokaryotic cells, such as *E. coli* cells, competent cells, which are prepared from exponentially growing bacteria using a standard $CaCl_2$ (or $MgCl_2$ or RbCl) method, can be transformed using standard methods. Transformation of bacterial cells can also be performed using protoplast fusion methods. In the case of eukaryotic cells, transfection can be carried out using calcium phosphate precipitation or conventional mechanical procedures, such as microinjection and electroporation, can be used. Also, the nucleic acid (e.g., contained in a plasmid) can be packaged in a liposome using standard methods. In the case of viral vectors, appropriate infection methods, which are well known in the art, can be used (see, e.g., Ausubel, et al., supra). In addition to being transfected with a nucleic acid encoding an FHF polypeptide of the invention, eukaryotic cells, such as mammalian cells, can be co-transfected with a second nucleic acid encoding a selectable marker, such as a neomycin resistance gene or the herpes simplex virus thymidine kinase gene. As is mentioned above, such selectable markers can facilitate selection of transformed cells.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

Antibodies, such as monoclonal and polyclonal antibodies, that specifically bind to FHF polypeptides (e.g., any or all of FHFs 1–4) are also included in the invention. These antibodies can be made by using an FHF polypeptide, or an FHF polypeptide fragment that maintain an FHF epitope, as an immunogen in standard antibody production methods (see, e.g., Kohler, et al., *Nature*, 256:495, 1975; Ausubel, et al., supra; Harlow and Lane, supra).

The term "antibody," as used herein, refers to intact immunoglobulin molecules, as well as fragments of immunoglobulin molecules, such as Fab, Fab', $(Fab')_2$, Fv, and SCA fragments, that are capable of binding to an epitope of an FHF polypeptide. These antibody fragments, which retain some ability to selectively bind to the antigen (e.g., an FHF antigen) of the antibody from which they are derived, can be made using well known methods in the art (see, e.g., Harlow and Lane, supra), and are described further, as follows.

(1) A Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) A $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as an FHF polypeptide, to which the paratope of an antibody, such as an FHF-4-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing FHF-specific antibodies include FHF polypeptides, e.g., any of FHFs 1–4, or FHF polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

FHF-specific polyclonal and monoclonal antibodies can be purified, for example, by binding to, and elution from, a matrix containing an FHF polypeptide, e.g., the FHF polypeptide (or fragment thereof) to which the antibodies were raised. Additional methods for antibody purification and concentration are well known in the art and can be practiced with the FHF-specific antibodies of the invention (see, for example, Coligan, et al., Unit 9, *Current Protocols in Immunology*, Wiley Interscience, 1994).

Anti-idiotype antibodies corresponding to FHF-specific antigens are also included in the invention, and can be produced using standard methods. These antibodies are raised to FHF-specific antibodies, and thus mimic FHF-specific epitopes.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

As is discussed above, because of their amino acid sequence homologies to previously identified FGF polypeptides (i e., FGFs 1–9), as well as their tissue localizations, FHFs are thought to play roles in regulating the development and function of the nervous system. Altered levels of FHFs, such as increased levels, may thus be associated with cell proliferative disorders, such as cell proliferative disorders of the nervous system. The term "cell-proliferative disorder" is used herein to describe conditions that are characterized by abnormally excessive cell growth, including malignant, as well as non-malignant, cell growth. Conversely, conditions characterized by inadequate cell growth may be characterized by decreased expression of FHFs. Accordingly, these conditions can be diagnosed and monitored by detecting the levels of FHFs in patient samples.

FHF-specific antibodies and nucleic acids can be used as probes in methods to detect the presence of an FHF polypeptide (using an antibody) or nucleic acid (using a nucleic acid probe) in a sample, such as a biological fluid (e.g., cerebrospinal fluid (CSF), such as lumbar or ventricular CSF) or a tissue sample (e.g., CNS tissue, e.g., neural tissue or eye tissue). In these methods, an FHF-specific antibody or nucleic acid probe is contacted with a sample from a patient suspected of having an FHF-associated disorder, and specific binding of the antibody or nucleic acid probe to the sample detected. The level of FHF polypeptide or nucleic acid present in the suspect sample can be compared with the level in a control sample, e.g., an equivalent sample from an unaffected individual, to determine whether the patient has an FHF-associated cell proliferative disorder. FHF polypeptides, or fragments thereof, can also be used as probes in diagnostic methods, for example, to detect the presence of FHF-specific antibodies in samples.

The FHF-specific nucleic acid probes can be labeled with a compound that facilitates detection of binding to the FHF nucleic acid in the sample. For example, the probe can contain biotinylated nucleotides, to which detectably labeled avidin conjugates (e.g., horseradish peroxidase-conjugated avidin) can bind. Radiolabeled nucleic acid probes can also be used. These probes can be used in nucleic acid hybridization assays to detect altered levels of FHFs in a sample. For example, in situ hybridization, RNAse protection, and Northern Blot methods can be used. Other standard nucleic acid detection methods that can be used in the invention are known to those of skill in the art (see, e.g., Ausubel, et al., supra). In addition, when the diagnostic molecule is a nucleic acid, it can be amplified prior to binding with an FHF-specific probe. Preferably, PCR is used, but other nucleic acid amplification methods, such as the ligase chain reaction (LCR), ligated activated transcription (LAT), and nucleic acid sequence-based amplification (NASBA) methods can be used.

Use of FHF-specific antibodies in diagnostic methods is described further, as follows. The antibodies of the invention can be used in vitro or in vivo for immunodiagnosis. The antibodies are suited for use in, for example, immunoassays in which they are in liquid phase or bound to a solid phase carrier (e.g., a glass, polystyrene, polypropylene, polyethylene, dextran, nylon, amylase, natural and modified cellulose, polyacrylamide, agarose, or magnetite carrier). The antibodies used in such immunoassays can be detectably labeled (e.g., with an enzyme, a radioisotope, a fluorescent compound, a colloidal metal, a chemiluminescent compound, a phosphorescent compound, or a bioluminescent compound) using any of several standard methods that are well known in the art. Examples of immunoassays in which the antibodies of the invention can be used include, e.g., competitive and non-competitive immunoassays, which are carried out using either direct or indirect formats. Examples of such immunoassays include radioimmunoassays (RIA) and sandwich assays (e.g., enzyme-linked immunosorbent assays (ELISAs)). Detection of antigens using the antibodies of the invention can be done using immunoassays that are run in either forward, reverse, or simultaneous modes, including immunohistochemical assays on physiological samples. Other immunoassay formats are well known in the art, and can be used in the invention (see, e.g., Coligan, et al., supra).

In addition to the in vitro methods described above, FHF-specific monoclonal antibodies can be used in methods for in vivo detection of an antigen, such as an FHF antigen (e.g., any one of FHFs 1–4). In these methods, a detectably labeled antibody is administered to a patient in a dose that is determined to be diagnostically effective by one skilled in the art. The term "diagnostically effective" is used herein to describe the amount of detectably labeled monoclonal antibody that is administered in a sufficient quantity to enable detection of the site having the antigen for which the monoclonal antibody is specific. As would be apparent to one skilled in the art, the concentration of detectably labeled monoclonal antibody that is administered should be sufficient so that the binding of the antibody to the cells containing the polypeptide is detectable, compared to background. Further, it is desirable that the detectably labeled monoclonal antibody is rapidly cleared from the circulatory system, to give the optimal target-to-background signal ratio.

The dosage of detectably labeled monoclonal antibodies for in vivo diagnosis will vary, depending on such factors as the age and weight of the individual, as well as the extent of the disease. The dosages can also vary depending on factors such as whether multiple administrations are intended, antigenic burden, and other factors known to those of skill in the art.

In addition to initial diagnosis, the FHF polypeptides, nucleic acids, and FHF-specific antibodies described above can be used in in vitro or in vivo methods for monitoring the progress of a condition associated with FHF expression. For example, they can be used in methods to monitor the course of amelioration of an FHF-associated disease, for example, after treatment has begun. In these methods, changes in the levels of an FHF-specific marker (e.g., an FHF polypeptide, an FHF nucleic acid, or an FHF-specific antibody) are detected, either in a sample from a patient or using the in vivo methods described above.

The invention also provides methods for treating conditions associated with altered expression of FHF polypeptides, for example, cell proliferative disorders (e.g., cell proliferative disorders of the central or peripheral nervous systems, for example, conditions affecting neural tissue, testes, heart tissue, and cells of the eye). Treatment of an FHF-associated cell proliferative disorder can be carried out, for example, by modulating FHF gene expression or FHF activity in a cell. The term "modulate" includes, for example, suppressing expression of an FHF when it is over-expressed, and augmenting expression of an FHF when it is under-expressed. In cases where a cell-proliferative disorder is associated with over-expression of an FHF, nucleic acids that interfere with FHF expression, at transcriptional or translational levels, can be used to treat the disorder. This approach employs, for example, antisense nucleic acids (i.e., nucleic acids that are complementary to, or capable of hybridizing with, a target nucleic acid, e.g., a nucleic acid encoding an FHF polypeptide), ribozymes, or triplex agents. The antisense and triplex approaches function by masking the nucleic acid, while the ribozyme strategy functions by cleaving the nucleic acid. In addition, antibodies that bind to FHF polypeptides can be used in methods to block the activity of an FHF.

The use of antisense methods to inhibit the in vitro translation of genes is well known in the art (see, e.g., Marcus-Sakura, *Anal. Biochem.*, 172:289, 1988). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see, e.g., Weintraub, *Scientific American*, 262:40, 1990). The antisense nucleic acids hybridize to corresponding nucleic acids, such as mRNAs, to form a double-stranded molecule, which interferes with translation of the mRNA, as the cell will not translate an double-stranded mRNA. Antisense nucleic acids used in the invention are typically at least 10–12 nucleotides in length, for example, at least 15, 20, 25, 50, 75, or 100 nucleotides in length. The antisense nucleic acid can also be as long as the target nucleic acid with which it is intended that it form an inhibitory duplex. As is described further below, the antisense nucleic acids can be introduced into cells as antisense oligonucleotides, or can be produced in a cell in which a nucleic acid encoding the antisense nucleic acid has been introduced by, for example, using gene therapy methods.

Introduction of FHF antisense nucleic acids into cells affected by a proliferative disorder, for the purpose of gene therapy, can be achieved using a recombinant expression vector, such as a chimeric virus or a colloidal dispersion system, such as a targeted liposome. Those of skill in this art know or can easily ascertain the appropriate route and means for introduction of sense or antisense FHF nucleic acids, without resort to undue experimentation.

Gene therapy methods can also be used to deliver genes encoding FHF polypeptides (e.g., any of FHFs 1–4) to cells. These methods can be carried out to treat conditions associated with insufficient FHF expression. Thus, these methods can be used to promote tissue repair or replacement, for example, in conditions including stroke, neurodegenerative diseases, such as Parkinson's disease and Alzheimer's disease, retinal degenerative diseases, such as retinitis pigmentosa and macular degeneration, and peripheral neuropathies.

Due to the high levels of expression of FHF-4 in the testes, there are a variety of applications for FHF-4-specific polypeptides, nucleic acids, and antibodies related to treating disorders of this tissue. Such applications include treatment of cell proliferative disorders related to FHF-4 expression in the testes. Various testicular developmental or acquired disorders can also be treated using FHF-4-related molecules. These conditions include, for example, viral infection (e.g., viral orchitis), autoimmunity, sperm production or dysfunction, trauma, and testicular tumors. The presence of high levels of FHF-4 in the testes also suggests that FHF-4, or an FHF-4 analogue, can be used to affect male fertility.

In addition to blocking mRNA translation, oligonucleotides, such as antisense oligonucleotides, can be used in methods to stall transcription, such as the triplex method. In this method, an oligonucleotide winds around double-helical DNA in a sequence-specific manner, forming a three-stranded helix, which blocks transcription from the targeted gene. These triplex compounds can be designed to recognize a unique site on a chosen gene (Maher, et al., *Antisense Res. and Dev.*, 1(3):227, 1991; Helene, *Anticancer Drug Design*, 6(6):569, 1991). Specifically targeted ribozymes can also be used in therapeutic methods directed at decreasing FHF expression.

The following examples are intended to illustrate, but not to limit, the invention. While the procedures described in the examples are typical of those that can be used to carry out certain aspects of the invention, other procedures known to those skilled in the art can also be used. The following materials and methods were used in carrying out the experiments described in the examples.

Materials and Methods

Random cDNA Sequencing. Details of retina cDNA library construction, template preparation, and sequence determination are described by Wang, et al., *J. Biol. Chem.* 271, 4468–4476, 1996.

Degenerate PCR. A fully degenerate sense strand primer, with a flanking EcoRI restriction site, was synthesized to correspond to the amino acid sequence VFENYYV (SEQ ID NO:27), and three partially degenerate antisense primers, with a flanking BamHI site, were synthesized to include all possible codons for the amino acid sequence MKGN(H/R)VK(SEQ ID NO:30). These primers were used to amplify human, murine, and bovine genomic DNA templates using *T. aquaticus* polymerase under the following conditions: 1×(94° C., 7 minutes), 35×(45° C., 2 minutes; 72° C., 0.5 minute; 94° C., 0.5 minutes; 95° C., 0.25 minutes). PCR products were cleaved with EcoRI and BamHI, fractionated by preparative agarose gel electrophoresis, subcloned into pBluescript, and sequenced individually.

cDNA and Genomic Clones. Oligo-dT primed cDNA libraries from adult human retinas (Nathans, et al., *Science* 232, 193–202, 1986) and P0–P7 mouse eyes were screened by DNA hybridization under standard conditions (see, e.g., Sambrook, et al., *Molecular Cloning: A Laboratory Manual*, 2nd Ed., Cold Spring Harbor Laboratory Press, Cold Spring Harbor, N.Y., 1989). The complete coding region sequences of human FHF-1, FHF-2, and FHF-3, and mouse FHF-1, FHF-3, and FHF-4 were obtained from two independent cDNA clones. For human FHF-4, the first 72 codons were sequenced from a single clone, and the rest of the coding region was sequenced from two independent clones. For mouse FHF-2, the coding sequence was determined from cloned genomic DNA and from a PCR product obtained by amplification of the full-length, coding region from the P0–P7 mouse eye cDNA library. A partial MboI digest of a mouse genomic DNA library in bacteriophage lambda was screened to obtain the mouse FHF-2 genomic clones.

Chromosomal Localization. Human chromosome mapping was performed by Southern blot analysis of DNA obtained from a panel of 24 human-mouse or human-hamster hybrid cell lines each carrying a different human chromosome (Oncor, Gaithersburg, Md.). Interspecific backcross progeny were generated by mating (C57BL/6J×*M. spretus*) F1 females and C57BL/6J males, as described (Copeland and Jenkins, *Trends Genet.* 7, 113–118, 1991). A total of 205 N2 mice were used to map the FHF loci. DNA isolation, restriction enzyme digestion, agarose gel electrophoresis, Southern blot transfer, and hybridization were performed essentially as described (Jenkins, et al., *J. Virol.* 43, 26–36, 1982), using Zetabind nylon membranes (AMF-Cuno). Washing was carried out to a final stringency of 0.8–1.0×SSCP, 0.1% SDS, at 65° C. The FHF-1 probe, a 1 kilobase fragment of mouse genomic DNA, detected fragments of 2.1 kilobases in C57BL/6J (B) DNA and 10.0 kilobases in *M. spretus* (S) DNA, following digestion with BamHI. The FHF-2 probe, a 0.75 kilobase fragment of mouse cDNA, detected BglI fragments of 19.0, 11.5, 8.2, and 2.2 kilobases (B) and 13.5, 8.2, and 2.2 kilobases (S). The FHF-4 probe, a 0.3 kilobase fragment of mouse cDNA, detected EcoRV fragments of approximately 24.0 kilobases (B) and 7.7 kilobases (S).

Most of the probes and RFLPs for the loci linked to the FHF genes in the interspecific backcross have been reported earlier. These include: Irg1 and Rap2a on chromosome 14 (Lee, et al., *Immunogenet.* 41, 263–270, 1995); Smst on chromosome 16 (Siracusa, et al., *Genetics* 127, 169–179, 1991); and Hprt, Cd401, and Ar on the X chromosome (Allen, et al, *Science* 259, 990–993, 1993; Fletcher, et al., *Genomics* 24, 127–132, 1994). The probe for apolipoprotein D (Apod), a 290 base pair HindIII/BamHI fragment of a rat cDNA that was provided by Alan Peterson, detected XbaI fragments of 3.1 and 2.8 kilobases (B) and 3.1 and 2.6 kilobases (S). The inheritance of the 2.6 kilobase *M. spretus*-specific XbaI RFLP was followed. Recombination distances were calculated as described (Green, in *Genetics and Probability in Animal Breeding Experiments* (Oxford Press, New York), pp. 77–113, 1981) using the computer program SPRETUS MADNESS. Gene order was determined by minimizing the number of recombination events required to explain the allele distribution patterns.

RNAse Protection. Total RNA was prepared from adult mouse brain, eye, heart, kidney, liver, lung, spleen, and testis by homogenization in guanidinium thiocyanate and extraction with phenol, followed by centrifugation through 5.7 M cesium chloride (Sambrook, et al., *Molecular Cloning: A Laboratory Manual,* 2nd Ed., Cold Spring Harbor Laboratory Press, Cold Spring Harbor, N.Y., 1989). Ten micrograms of total RNA from each tissue, or ten micrograms of yeast tRNA, was used for the RNAse protection assay. Riboprobes were synthesized using either T7 or T3 RNA polymerase on linearized templates that were cloned in pBluescript. Each mouse FHF probe contained 150–250 nucleotides from the antisense strand, linked to 25–50 nucleotides of vector sequence. Reagents were obtained from Ambion (Austin, Tex.), and the hybridization and digestion conditions used were as recommended by Ambion.

In Situ Hybridization. Freshly dissected adult mouse brains, whole embryos, or heads were rapidly frozen in plastic molds placed on a dry ice/ethanol slurry and processed for sectioning as previously described (Cole, et al., *J. Neurochem.* 55, 1920–1927, 1990). $^{33}$P-labeled antisense riboprobes were prepared from linearized pBluescript plasmid subclones, using either T3 or T7 RNA polymerase. In situ hybridization was performed in 50% formamide, 0.3 M NaCl at 56° C., as described (Saffen, *Proc. Natl. Acad. Sci. USA* 85, 7795–7799, 1988). Following RNAse treatment, the slides were washed for 1 hour in 0.1×SSC at 55° C. After the hybridized sections were exposed to X-ray film, the slides were stained with cresyl violet. Digitized images of the stained slides and corresponding autoradiograms were superimposed using Adobe Photoshop software. The probes used were: FHF-1, 0.75 kilobase containing the complete coding region; FHF-2, 0.5 kilobase containing 0.3 kilobase of intron 4 and 0.2 kilobase of exon 5; FHF-3, two 0.4 kilobase segments containing the 5' or 3' halves of the coding region; and FHF-4, 0.5 kilobase containing the 3' two-thirds of the coding region. The coding regions of the different murine FHFs share between 63% and 71% nucleotide sequence identity, suggesting that there should be little or no cross-hybridization under the conditions used.

Immunohistochemistry. Rabbit polyclonal anti-FHF-1 antibodies were raised against a bacterial fusion protein consisting of the carboxyl-terminal 190 amino acids of FHF-1 fused to the T7 gene 10 protein (Studier, et al., *Meth. Enzymol.* 185, 60–89, 1980). Anti-FHF-1 antibodies were affinity purified using the fusion protein immobilized on nitrocellulose as an affinity matrix, and antibodies directed against the fusion partner were removed by absorption onto immobilized T7 gene 10 protein. For immunostaining of primate brain samples, three monkeys (*Macaca mulatta*) were anesthetized with Ketamine (35 mg/kg, i.m.), injected with a lethal dose of sodium pentobarbital (100 mg/kg, i.v.), and perfused through the heart with 4% paraformaldehyde in 0.1 M phosphate buffer (pH 7.4). The brains were removed, cryoprotected in 20% sucrose at 4° C., frozen, and cut at a thickness of 10 or 20 µm. Sections were sequentially incubated with affinity purified-rabbit anti-FHF-1 antibodies, biotinylated goat anti-rabbit IgG (Vector), peroxidase-conjugated avidin (Extravidin, Sigma Chemical Co.), and 3,3'-diaminobenzidine dihydrochloride (Aldrich), in the presence of hydrogen peroxide. Most sections were then mounted on gelatin-coated slides, dehydrated, cleared, and covered with a cover-slip. Following the histochemical reaction, some of the 10 µm-thick sections were washed and incubated sequentially in mouse anti-parvalbumin (Sigma), biotinylated horse anti-mouse IgG (Vector), and streptavidin conjugated to Texas Red (Chemicon). These sections were mounted on clean slides, partially dried, and covered in a glycerol/phosphate buffer medium. Adjacent sections were processed histochemically for cytochrome oxidase or were stained for Nissl substance, to determine the boundaries of subcortical nuclei or cortical areas and layers.

Production and Localization of FHF-1 in Transfected Cells. To increase the efficiency of FHF-1 translation, the region immediately 5' to the initiator methionine coding sequence was converted to an optimal ribosome binding site (CCACCATGG) by PCR amplification, before inserting the complete FHF-1 open reading frame into the eukaryotic expression vector pCIS (Gorman, et al., *DNA Protein Eng. Tech.* 2, 3–10, 1990). The pCIS vector was also used for the beta-galactosidase constructs. Human embryonic kidney cells (293 cells) were transiently transfected with the expression construct and a plasmid expressing the simian virus 40 (SV40) large T-antigen (pRSV-TAg) using the calcium phosphate method (Gorman, et al., supra). For $^{35}$S-methionine labeling, cells were transferred to serum-free medium 24 hours after transfection, and labeled for 6 hours. For immunostaining, transfected cells were grown on gelatin-coated coverslips. One day after transfection, the cells were fixed in 2% formaldehyde in PBS for 30 minutes at room temperature, permeabilized with cold methanol for 10 minutes at −20° C., preincubated for 15 minutes in 3% BSA in phosphate-buffered saline (PBS), incubated for 1 hour at room temperature with affinity purified anti-FHF-1 antibody at a dilution of 1:1000 and mouse monoclonal anti-BiP at a dilution of 1:400 in 3% BSA in PBS, washed 3×15 minutes with 0.1% TWEEN-20™ in PBS at room temperature, and then incubated with fluorescein-conjugated donkey anti-rabbit IgG and rhodamine-conjugated goat anti-mouse IgG in 3% BSA in PBS for 30–60 minutes. The coverslips were then washed in 0.1% TWEEN-20™ in PBS and mounted in 0.1% 1,4-diazobicyclo-[2,2,2]-octane (DABCO), 75% glycerol, 10 mM Tris, pH 8.0. For X-gal staining, transfected cells were fixed in 0.5% glutaraldehyde/PBS for 10 minutes at room temperature, washed twice in PBS with 2 mM MgCl$_2$, incubated in 1 mg/ml 5 mM K$_3$Fe(CN)$_6$, 5 mM K$_4$Fe(CN)$_6$, 2 mM MgCl$_2$ in PBS for 1–2 hours at 37° C. and postfixed in 0.5% glutaraldehyde in PBS for 10 minutes at room temperature.

EXAMPLE 1

Identification of Fibroblast Growth Factor Homologous Factors (FHFs)

To identify gene products expressed in the human retina, random segments of human retina cDNA clones were partially sequenced, and the resulting partial sequences were compared to sequences in publicly available databases. In detail, an adult human retina cDNA library constructed in lambda gt10 (Nathans, et al., *Science*, 232:193, 1986) was amplified, and the cDNA inserts were excised en mass by cleavage with EcoRI and purified from the vector by agarose gel electrophoresis. Following heat denaturation of the purified cDNA inserts, a synthetic oligonucleotide having an EcoRI site at its 5' end and six random nucleotides at its 3' end (5'-GACGAGATATTAGAATTCTACTCGNNNNNN-3'; (SEQ ID NO:32)) was used to prime two sequential rounds of DNA synthesis in the presence of the Klenow fragment of *E. Coli* DNA polymerase. The resulting duplex DNA molecules were amplified by the polymerase chain reaction (PCR) using a primer corresponding to the unique 5' flanking sequence (5'-CCCCCCCCCGACGAGATATT-AGAATTCTACTCG-3'; (SEQ ID NO:33)). The PCR products, representing a random sampling of the original cDNA inserts, were cleaved with EcoRI, size fractionated by preparative agarose gel electrophoresis to include only segments of approximately 500 base pairs in length, and cloned into lambda gt10. Three thousand single plaques from this library were arrayed in 96-well trays and the inserts from these clones were amplified by PCR and then sequenced using the dideoxy method and automated fluorescent detection (Applied Biosystems). A single sequencing run from one end of each insert was conceptually translated for both strands, in all three reading frames, and the six resulting amino acid sequences were used to search for homology in the GenBank nonredundant protein database using the BLASTX searching algorithm.

One partial cDNA sequence was identified that showed statistically significant homology to previously described members of the FGF family. Using this partial cDNA as a probe, multiple, independent cDNA clones were isolated from the human retina cDNA library, including two clones that encompass the entire open reading frame, and from which complete nucleotide sequences were determined. The complete nucleotide sequence encodes a novel and highly divergent member of the FGF superfamily, and was designated fibroblast growth factor homologous factor-1 (FHF-1). The deduced amino acid sequence of FHF-1 contains 244 amino acids and is 27% identical to FGF-9, which is the member of the FGF family that shares the most homology with FHF-1. The nucleotide and deduced amino acid sequences of FHF-1 are shown in FIG. 5.

The FHF-1 sequence was used to search the National Center for Biotechnology Information (NCBI) database of expressed sequence tags (ESTs) and sequence tagged sites (STSs). One EST entry (DBEST ID 06895), derived from a human infant brain cDNA library (Adams, et al., *Nature Genet.* 4, 373–380, 1993) encoded a segment of 77 amino acids having significant homology to the carboxyl-terminus of FHF-1, but no significant homology to other members of the FGF family. The polypeptide containing this amino acid segment was designated FHF-2. One STS entry (DBEST ID 76387; Brody, et al., *Genomics* 25, 238–247, 1995), derived from human genomic DNA contained a putative exon encoding a protein segment with a high degree of homology to FHF-1 and a low degree of homology to other FGF family members. The polypeptide containing this amino acid segment was designated FHF-3. Full-length FHF-2 and FHF-3 cDNA clones were isolated from an adult human retina cDNA library, and were found to encode proteins of 245 and 225 amino acids, respectively, each having greater than 58% amino acid identity to FHF-1 and to each other. The nucleotide and deduced amino acid sequences of FHF-2 and FHF-3 are shown in FIG. 6 and FIG. 7, respectively.

A comparison of the sequences of FHF-1, FHF-2, and FHF-3 revealed several regions of high amino acid sequence conservation, and two of these regions were used to design degenerate oligonucleotide primers for use in PCR. The primers have sequences that correspond to codons for the conserved amino acids at their 3' ends (at residues 151–157 and 184–190 in the FHF-1 sequence (SEQ ID NO:1); see FIG. 5, and below), and restriction enzyme cleavage sites at their 5' ends, to facilitate cloning of the resulting PCR products. A full degenerate sense strand primer with a flanking EcoRI restriction site was synthesized for the amino acid sequence VFENYYV (SEQ ID NO:27; amino acids 151–157)(5'-CCGATCGAATTCGTNTT(T/C)GA(A/G)AA(T/C)TA(T/C)TA(T/C)GT-3'; SEQ ID NO:34). Three partially degenerate antisense primers with a flanking BamHI site were synthesized to include all possible codons for the amino acid sequence MKGN(H/R)VK(SEQ ID NO:30; amino acids 184–190)
(5'-GCGATCGGATCCTTNAC(A/G)TG(A/G)TTNCC(T/C)TTCAT-3'(SEQ ID NO:35);
5'-GCGATCGGATCCTTNAC(T/C)CT(A/G)TTNCC(T/C)TTCAT-3'(SEQ ID NO:36); and
5'-GCGATCGGATCCTTNACNCG(A/G)TTNCC(T/C)TTCAT-3'(SEQ ID NO:37)).

The three pairs of sense and anti-sense primers were used in PCR reactions containing human, murine, and bovine genomic DNA templates and *Thermus aquatics* DNA polymerase and the reactions were carried out under the following conditions: 1×(94° C., 7 minutes), 35×(45° C., 2 minutes; 72° C., 0.5 minutes; 94° C., 0.5 minutes; 95° C., 0.25 minutes). PCR products were cleaved with EcoRI and BamHI, fractionated by preparative agarose gel electrophoresis, subcloned into pBluescript, and individually sequenced. Analysis of the amplification products obtained using mouse, human, and bovine genomic DNA templates revealed that, in each of these species, this region of FHF-1, FHF-2, and FHF-3 is encoded within a single exon. This analysis also revealed a fourth class of FHF-like PCR products which was present in all three species and was found to encode an FHF-like protein, designated FHF-4. The PCR product corresponding to FHF-4 was used as a probe to isolate full-length cDNA clones from a human retina cDNA library and a developing mouse eye cDNA library. A protein of 247 amino acids having greater than 60% amino acid identity to FHF-1, FHF-2, and FHF-3, is predicted to be encoded by these clones. The nucleotide and deduced amino acid sequence of FHF-4 is shown in FIG. 8.

FIG. 3 shows an alignment of the amino acid sequences of identified FHFs and previously characterized and published FGFs (1–9) and FIG. 4 is a dendrogram of the identified FHFs and all the published FGF sequences. Pairwise comparisons between each FHF and the nine FGF family members show less than 30% amino acid sequence identity, while all pairwise comparisons among the four FHFs show between 58% and 71% amino acid sequence identity. Between mouse and human orthologues, there is greater than 97% amino acid sequence identity. The murine FHFs differ from their human orthologues by the amino acid substitutions listed below. The first and last letters indicate the amino acids in the human and mouse sequences, respectively, and the number indicates the position along the polypeptide chain: FHF-1: Q86E; FHF-2: A2T, L136H; FHF-3: A58T, P60Q, Q180R, L197V, Q207R, A217T, P225H; and FHF-4: C40F, A181V, P221A, S244C. Thus, the four FHFs define a distinct and highly conserved branch of the FGF family.

FHFs 1–4 each lack a recognizable amino-terminal signal sequence. Among the nine previously characterized members of the FGF family, FGF-1, FGF-2, and FGF-9 are also distinguished by lacking a recognizable amino-terminal signal sequence (Abraham, et al., *Science* 233, 545–548, 1986; Jaye, et al., *Science* 233, 541–545, 1986; Miyamoto, et al., *Mol. Cell Biol.* 13, 4251–4259, 1993). Current evidence indicates that FGF-1 and FGF-2 are synthesized in the cytosol and are released by a mechanism independent of the ER-Golgi secretory pathway (Florkiewicz, et al., *J. Cell Physiol.* 162, 388–399, 1995; Jackson, et al., *J. Biol. Chem.* 270, 33–36, 1995). Although FGF-9 lacks a cleavable amino-terminal signal sequence, it is glycosylated and is efficiently secreted from cultured glioma, Chinese hamster ovary, and COS cells, presumably via the ER-Golgi pathway (Miyamoto, et al., *Mol. Cell Biol.* 13, 4251–4259, 1993).

EXAMPLE 2

Deduced Amino Acid Sequence of FHF-4

FIG. 8 shows the nucleotide and deduced amino acid sequences of human FHF-4, which was derived from the human retina cDNA clones described above. As is mentioned above, the primary translation product of the human FHF-4 gene is predicted to be 247 amino acids in length. The human FHF-4 initiator methionine codon shown in FIG. 8 at nucleotide positions 78–80 and is the first in frame ATG; a good consensus ribosome binding site (CCACC<u>ATG</u>G; Kozak, *Nucleic Acids Res.*, 15:8125, 1987) is found at this position. This choice of ATG conforms to the sites of translation initiation in FHF-1, FHF-2, and FHF-3, as shown in the alignment in FIG. 1. The next methionine codon in the FHF-4 open reading frame is located 85 codons 3' to the putative initiator methionine codon. Similar to FGF-1 and FGF-2, as well as FHFs 1–3, FHF-4 lacks a discernable amino-terminal signal sequence. Human FHF-4 has a single Asn-Lys-Ser motif at amino acids 242–244, which conforms to the consensus sequence for asparagine-linked glycosylation, but this site is not conserved in the highly homologous mouse FHF-4 sequence (see FIG. 3), suggesting that it may not be used for glycosylation.

EXAMPLE 3

Chromosomal Localization of FHF Genes

In humans, FHF-1, FHF-2, FHF-3, and FHF-4 are located on chromosomes 3, X, 17, and 13, respectively. The chromosomal locations of FHF-1, FHF-2, and FHF-4, were determined by Southern blot hybridization of genomic DNA from rodent-human hybrid cell lines carrying individual human chromosomes. For example, in the case of human FHF-4, a Southern blot containing restriction enzyme-digested DNA from a panel of 24 human-mouse and human-hamster cell line, each containing a different human chromosome (Oncor, Gaithersburg, Md). Hybridization of a human FHF-4 probe to human, mouse, and hamster genomic DNA produced distinct hybridizing fragment sizes. Among the hybrid panels, the human-specific hybridization pattern was seen in the lanes corresponding to the hybrid cell line carrying human chromosomes 1 and 13, suggesting that one of these cell lines contains additional genomic sequences derived from the chromosome present in the other cell line. To determine which of these two human chromosomes contained the FHF-4 gene, the location of the mouse gene was determined by interspecific backcross mapping. As discussed further below, this analysis located the FHF-4 gene on mouse chromosome 14, less than 1 cM from the Rap2a gene, and within a region that is syntenic with human chromosome 13q34. Taken together, these data show that in humans, the FHF-4 gene maps to chromosome 13. The FHF-3 locus is on human chromosome 17, as the STS described above that encompasses one exon of FHF-3 was derived from human chromosome 17 and maps near the BRCA-1 gene (Brody, et al., *Genomics* 25, 238–247, 1995).

The chromosomal locations of FHF-1, FHF-2, and FHF-4 in the mouse were determined using an inter-specific backcross mapping panel from crosses of (C57BL/6J×*Mus spretus*), F1×C57BL/6J. This mapping panel has been typed for over 2100 loci, which are well distributed over all 19 mouse autosomes and the X-chromosome (Copeland and Jenkins, *Trends Genet.* 7, 113–118, 1991). C57BL/6J and *M. spretus* DNAs were digested with several restriction enzymes and analyzed by Southern blot hybridization for informative RFLPs. The chromosomal location of each locus was determined by comparing its strain distribution in the backcross mice with the strain distribution patterns for all other loci already mapped in the backcross (FIG. 9). FHF-1 mapped to the proximal region of mouse chromosome 16, 1.6 cM distal to Smst and 5.1 cM proximal to Apod. FHF-2 mapped to the X chromosome, and did not recombine with Cd401 in 168 mice typed in common, suggesting that the two loci are within 1.8 cM of each other (upper 95% confidence interval). As is mentioned above, FHF-4 mapped to the distal region of chromosome 14, and did not recombine with Rap2a in 142 mice typed in common, suggesting that the two loci are within 2.1 cM of each other. The FHF-3 gene was not mapped with the backcross panel, as it did not reveal an informative RFLP when tested with 14 restriction enzymes. The proximity of the human FHF-3 gene to BRCA-1 suggests that the mouse FHF-3 gene resides on chromosome 11 in the region that is syntenic with the BRCA-1 region of human chromosome 17. The FHF genes map in regions of the composite mouse linkage map (Mouse Genome Database, Jackson Laboratory, Bar Harbor, Me.), which contains a number of mutations that may be candidate FHF alleles.

EXAMPLE 4

Tissue and Subcellular Distributions of FHF RNAs

Expression Patterns of FHFs in the Mouse. The tissue distributions of transcripts derived from each of the four identified FHF genes were determined in RNAse protection experiments. Analysis of RNA prepared from brain, eye, heart, kidney, liver, lung, spleen, and testis revealed that each FHF is expressed in the brain, and FHF-1, FHF-2, and FHF-3 are expressed in the eye, FHF-1 and FHF-4 are expressed in the testis, and FHF-2 is expressed in the heart (FIG. 10). In the brain, FHF-2 transcripts are at least five-fold more abundant than the transcripts from any of the other FHFs.

Figure 11A:
Figures 11B, 11C:
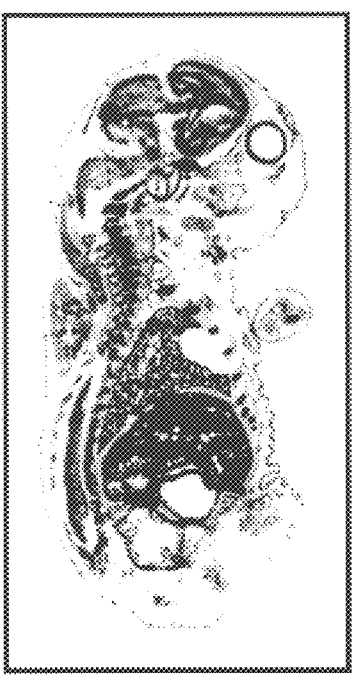
Figure 11D:
Figure 11E:
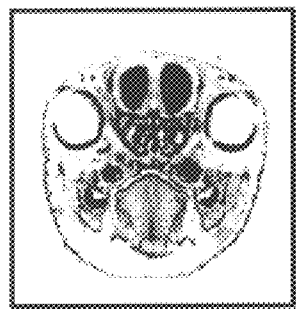
Figure 11F:
Figure 11G:
Figure 11H:
Figure 11I:
Figure 11L:
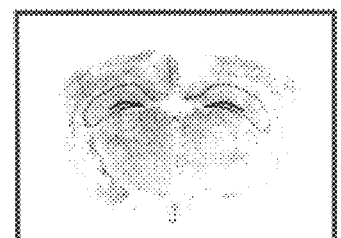
Figure 11J:
Figure 11K:

The patterns of FHF gene expression during development were studied by in situ hybridization experiments using sections obtained on gestational day 11 (e11), gestational day 17 (e17), postnatal day 1 (P1), and from adults. FHF-2 transcripts are abundant at each of the time points examined, and are present in all divisions of the central and peripheral nervous systems, including the enteric nervous system (FIGS. 11A, 11C, 11D, and 11F). Consistent with the RNAse protection experiments, FHF-2 transcripts were observed in the developing heart at e17 (FIG. 11D). FHF-1, FHF-3, and FHF-4 transcripts were also observed to be widely distributed throughout the developing nervous system (FIGS. 11B and 11E). For example, at P1, FHF-1 was found to be highly expressed in the retina, olfactory epithelium, and olfactory bulb (FIG. 11E). At e11, FHF-1 and FHF-3 were also found in a segmental pattern in the body wall (FIG. 11B). In the adult brain, each FHF showed a distinct pattern of expression: FHF-1 transcripts were present at high levels in the olfactory bulb, and at lower levels in the cerebellum, the deep cerebellar nuclei, throughout the cortex, and in multiple midbrain structures (FIG. 11G); FHF-2 transcripts were most abundant in the hippocampus and were present at lower levels in multiple brain areas (FIGS. 11H and 11I); FHF-3 transcripts were present in the olfactory bulb, hippocampus, and cerebellum, where they were most concentrated in the Purkinje cell layer (FIG. 11J); and FHF-4 transcripts are present at high levels throughout the granular layer of the cerebellum, and at lower levels in the hippocampus and olfactory bulb (FIGS. 11K and 11L).

Distribution of FHF-1 Immunoreactivity in Monkey Brain. The distribution of FHF-1 immunoreactivity in adult rhesus monkey brain was examined using affinity purified polyclonal anti-FHF-1 antibodies. These antibodies bind to recombinant FHF-1, but do not bind to recombinant FHF-2, as was determined by immunostaining of transfected 293 cells and by Western blotting. Although immunoreactivity with these antibodies is referred to as 'FHF-1 immunoreactivity' the possibility exists that other members of the FHF family are in part responsible for the observed immunostaining.

FHF-1 immunoreactive somata are present throughout the rhesus monkey cerebral cortex, but they are unevenly distributed across layers in any one area and display marked variations in density and distribution across functional areas (FIGS. 12A–12E). The low magnification photomicrographs in FIG. 12 show that in primary visual, somatosensory, and auditory areas, a relatively high density of immunostained cells is present and that these cells occupy predominantly the middle layers. In contrast, fewer and more widely scattered immunostained neurons are present in the precentral motor area and in the association cortex of the superior parietal lobule.

Common to each of these cortical areas is the presence of several FHF-1 immunoreactive populations, the most prominent of which have relatively large (12–14 $\mu$m diameter), intensely immunoreactive somata. Other neurons with smaller (8–10 $\mu$m diameter) and more lightly immunostained somata are also present in all areas (FIG. 12F). Colocalization experiments demonstrated that the FHF-1 immunoreactive neurons in the cerebral cortex make up a subpopulation of neurons that are immunoreactive for the calcium-binding protein, parvalbumin (FIGS. 12G and 12H), which have previously been shown to make up a subset of gabanergic interneurons in the monkey cerebral cortex (Hendry, et al., *Exp. Brain Res.* 76, 467–472, 1989). Variations in immunostained cell density were also seen in the hippocampal formation, where intensely immunoreactive somata were relatively common in the subicular complex, but were widely scattered in the CA fields, the dentate hilus, and the dentate gyrus (FIG. 12I).

A different pattern of FHF-1 immunostaining was seen in the dorsal thalamus (FIG. 12J). Only a few of the many nuclei in this region contained immunoreactive neurons; most prominent among them was the principal somatosensory relay nucleus (the caudal ventroposterolateral nucleus, VPLc) and the visual relay nucleus (the lateral geniculate nucleus, LGN). In the LGN, both magnocellular and parvicellular layers are equally immunostained. FIG. 12J shows that in the LGN, ipsilateral to an eye deprived by occlusion since birth, FHF-1 immunostaining was markedly lower in layers innervated by the deprived eye than in layers innervated by the normal eye.

The relatively large sizes of the FHF-1 immunostained somata in nuclei of the dorsal thalamus suggests they are cell bodies of neurons that send their axons to the cerebral cortex. Localization of FHF-1 immunoreactivity in neurons of VPLc and LGN that are lightly immunoreactive for parvalbumin supports this conclusion, since these parvalbumin immunostained neurons in dorsal thalamus have been shown to be thalamocortical neurons (Jones and Hendry, *Eur. J. Neurosci.* 1, 222–246, 1989).

Outside of the dorsal thalamus, FHF-1 immunoreactive neurons were present in a diverse collection of subcortical nuclei, including the globus pallidus and putamen, red nucleus, substantia nigra, and third nerve complex (FIG. 12K). In addition, large cells in the deep layers of both the superior and inferior colliculi were immunostained, as were neurons in the deep cerebellar nuclei. In conclusion, FHF-1 immunoreactivity was broadly distributed across the neuraxis, but at each level it was present in subsets of neurons.

Subcellular Localization of FHF-1 in Transfected Cells. As noted above, of the nine FGFs described prior to this report, FGF-1 and FGF-2 are distinguished by lacking of an amino terminal signal sequence and by secretion via a pathway that is independent of the ER and Golgi apparatus (Florkiewicz, et al., *J. Cell Physiol.* 162, 388–399, 1995; Jackson, et al., *J. Biol. Chem.* 270, 33–36, 1995). Moreover, FGF-1 and a subset of FGF-2 isoforms, produced by alternative translation initiation, have been shown to accumulate in the nuclei of the cells in which they are synthesized, as well as in the nuclei of target cells (Imamaura, et al., *Science* 249, 1567–1570, 1990; Imamaura, et al., *J. Biol. Chem.* 267, 5676–5679, 1992; Bugler, et al., *Molec. Cell Biol.* 11, 573–577, 1991; Zhan, et al., *Biochem. Biophys. Res. Comm.* 188, 982–991, 1992; Cao, et al., *J. Cell Science* 104, 77–87, 1993; Wiedlocha, et al., *Cell* 76, 1039–1051, 1994). These proteins contain a nuclear localization signal (NLS) that conforms closely to a consensus NLS. The nuclear accumulation of FGF-1 and FGF-2 has raised the possibility that these proteins have modes of action in addition to those mediated by binding and activating cell surface receptors.

Like FGF-1 and FGF-2, each of the four identified FHFs lacks a classical signal sequence and contains clusters of basic residues near its amino terminus that could serve as an NLS. These observations suggest that FHFs may resemble FGF-1 and FGF-2 in their mechanism of secretion and in their subcellular localization. To test this possibility, the fate of FHF-1 synthesized in transiently transfected 293 cells, which are human embryonic kidney cells, was determined. In one set of experiments, biosynthetically labeled FHF-1 was found to accumulate to high levels intracellularly, but was not detectably secreted into the medium (FIG. 13). In contrast, human growth hormone produced in parallel transfections was efficiently secreted (FIG. 13). As 293 cells can secrete a wide variety of growth factors through the ER-Golgi pathway, this experiment is consistent with the proposal that FHFs are not secreted via this route.

In a second set of experiments, immunostaining of transfected 293 cells revealed accumulation of FHF-1 in the nucleus, suggesting that the clusters of basic residues can function as an NLS. A similar result was obtained with FHF-2. Two main classes of NLS motifs have been described, the classical and bipartite motifs (Boulikas, *Crit. Rev. Eukaryotic Gene Expression* 3, 193–227, 1993). The classical NLS contains a cluster of six lysine or arginine amino acids, and the bipartite NLS contains two clusters of three or four basic amino acids separated by a ten amino acid spacer. In FHF-1 the clusters of basic amino acids resemble more closely the bipartite NLS consensus. To identify and characterize the putative FHF-1 NLS, we determined the subcellular localization of deletion mutants of FHF-1 by immunostaining with anti-FHF-1 antibodies, and of fusions between FHF-1 and β-galactosidase by X-gal staining. These experiments show that the two clusters of arginines and lysines at amino acids 11–18 and 28–38 in FHF-1 make up the two basic regions of a bipartite NLS. In the context of the FHF-1 protein, deletion of either cluster produced a modest increase in the level of cytoplasmic FHF-1, but left significant nuclear accumulation (constructs 2 and 3; FIG. 14), while deletion of both regions abolished nuclear accumulation (construct 4; FIGS. 14 and 15). To further characterize the minimal region required for import, the first 56 or the first 69 residues of FHF-1 were fused to beta-galactosidase and were shown to contain a functional NLS (constructs 5 and 6; FIGS. 14 and 15). Fusion of FHF-1 amino acids 1–22 or 23–55 individually to beta-galactosidase failed to direct nuclear localization, indicating a requirement for both parts of the bipartite NLS or a requirement for sequences distal to the first 55 residues. With beta-galactosidase fused to the first 69 amino acids of FHF-1, the results of a deletion analysis resembled those seen with intact FHF-1 (constructs 5, 9, 10, and 11; FIGS. 14 and 15). Finally, fusion of FHF-1 amino acids 11–38, containing only the two clusters of basic amino acids separated by a 10 amino acid spacer, conferred nuclear localization, although less efficiently than the larger segments that contained this region, suggesting that amino acids 1–10 or 56–68, outside of the bipartite NLS consensus, play an ancillary role in nuclear localization.

It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

We claim:

1. An isolated polynucleotide encoding fibroblast growth factor homologous factor-4 (FHF-4) polypeptide having the amino acid sequence of SEQ ID NO: 4.

2. An isolated polynucleotide selected from the group consisting of:

a) SEQ ID NO: 21;

b) SEQ ID NO: 21, wherein each T is replaced with a U; and c) nucleic acid sequences fully complementary to a) or b).

3. An expression vector comprising a polynucleotide of claim 1.

4. The vector of claim 3, wherein the vector is a plasmid.

5. The vector of claim 3, wherein the vector is a virus.

6. A host cell stably transformed with the vector of claim 3.

7. The host cell of claim 6, wherein the cell is prokaryotic.

8. The host cell of claim 6, wherein the cell is eukaryotic.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 243 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

Met Ala Ala Ala Ile Ala Ser Ser Leu Ile Arg Gln Lys Arg Gln Ala
1               5                   10                  15

Arg Glu Ser Asn Ser Asp Arg Val Ser Ala Ser Lys Arg Arg Ser Ser
                20                  25                  30

Pro Ser Lys Asp Gly Arg Ser Leu Cys Glu Arg His Val Leu Gly Val
                35                  40                  45

Phe Ser Lys Val Arg Phe Cys Ser Gly Arg Lys Arg Pro Val Arg Arg
        50                  55                  60

Arg Pro Glu Pro Gln Leu Lys Gly Ile Val Thr Arg Leu Phe Ser Gln
65                  70                  75                  80

Gln Gly Tyr Phe Leu Gln Met His Pro Asp Gly Thr Ile Asp Gly Thr
                85                  90                  95

Lys Asp Glu Asn Ser Asp Tyr Thr Leu Phe Asn Leu Ile Pro Val Gly
                100                 105                 110

Leu Arg Val Val Ala Ile Gln Gly Val Lys Ala Ser Leu Tyr Val Ala
            115                 120                 125

Met Asn Gly Glu Gly Tyr Leu Tyr Ser Ser Asp Val Phe Thr Pro Glu
        130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Ile

-continued

```
                180                 185                 190
Lys Pro Ser Ser His Phe Val Pro Lys Pro Ile Glu Val Cys Met Tyr
            195                 200                 205
Arg Glu Pro Ser Leu His Glu Ile Gly Glu Lys Gln Gly Arg Ser Arg
        210                 215                 220
Lys Ser Ser Gly Thr Pro Thr Met Asn Gly Gly Lys Val Val Asn Gln
225                 230                 235                 240
Asp Ser Thr
```

(2) INFORMATION FOR SEQ ID NO:2:

(i) SEQUENCE CHARACTERISTICS:
        (A) LENGTH: 245 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Met Ala Ala Ile Ala Ser Ser Leu Ile Arg Gln Lys Arg Gln Ala
1               5                  10                  15
Arg Glu Arg Glu Lys Ser Asn Ala Cys Lys Cys Val Ser Ser Pro Ser
            20                  25                  30
Lys Gly Lys Thr Ser Cys Asp Lys Asn Lys Leu Asn Val Phe Ser Arg
        35                  40                  45
Val Lys Leu Phe Gly Ser Lys Arg Arg Arg Arg Pro Glu Pro
50                  55                  60
Gln Leu Lys Gly Ile Val Thr Lys Leu Tyr Ser Arg Gln Gly Tyr His
65                  70                  75                  80
Leu Gln Leu Gln Ala Asp Gly Thr Ile Asp Gly Thr Lys Asp Glu Asp
                85                  90                  95
Ser Thr Tyr Thr Leu Phe Asn Leu Ile Pro Val Gly Leu Arg Val Val
            100                 105                 110
Ala Ile Gln Gly Val Gln Thr Lys Leu Tyr Leu Ala Met Asn Ser Glu
        115                 120                 125
Gly Tyr Leu Tyr Ile Ser Glu Leu Phe Thr Pro Glu Cys Lys Phe Lys
130                 135                 140
Glu Ser Val Phe Glu Asn Tyr Tyr Val Ile Tyr Ser Ser Met Ile Tyr
145                 150                 155                 160
Arg Gln Gln Gln Ser Gly Arg Gly Trp Tyr Leu Gly Leu Asn Lys Glu
                165                 170                 175
Gly Glu Ile Met Lys Gly Asn His Val Lys Lys Asn Lys Pro Ala Ala
            180                 185                 190
His Phe Leu Pro Lys Pro Leu Lys Val Ala Met Tyr Lys Glu Pro Ser
        195                 200                 205
Leu His Asp Leu Thr Glu Phe Ser Arg Ser Gly Ser Gly Thr Pro Thr
210                 215                 220
Lys Ser Arg Ser Val Ser Gly Val Leu Asn Gly Gly Lys Ser Met Ser
225                 230                 235                 240
His Asn Glu Ser Thr
                245
```

(2) INFORMATION FOR SEQ ID NO:3:

(i) SEQUENCE CHARACTERISTICS:
        (A) LENGTH: 225 amino acids
        (B) TYPE: amino acid (C) STRANDEDNESS: Not Relevant
(D) TOPOLOGY: linear (ii) MOLECULE TYPE: protein (xi) SEQUENCE DESCRIPTION: SEQ ID NO:3:

```
Met Ala Leu Ala Ser Ser Leu Ile Arg Gln Lys Arg Glu Val Arg
1               5                   10                  15

Glu Pro Gly Gly Ser Arg Pro Val Ser Ala Gln Arg Arg Val Cys Pro
            20                  25                  30

Arg Gly Thr Lys Ser Leu Cys Gln Lys Gln Leu Leu Ile Leu Ile Ser
                35                  40                  45

Lys Val Arg Leu Cys Gly Gly Arg Pro Ala Arg Pro Asp Arg Gly Pro
50                  55                  60

Glu Pro Gln Leu Lys Gly Ile Val Thr Lys Leu Phe Cys Arg Gln Gly
65                  70                  75                  80

Phe Tyr Leu Gln Ala Asn Pro Asp Gly Thr Ile Asp Gly Thr Lys Asp
                85                  90                  95

Glu Asn Ser Ser Phe Thr His Phe Asn Leu Ile Pro Val Gly Leu Arg
                100                 105                 110

Val Val Ile Ile Gln Ser Ala Lys Leu Gly His Tyr Met Ala Met Asn
            115                 120                 125

Ala Glu Gly Leu Asp Tyr Ser Ser Pro His Phe Thr Ala Glu Cys Arg
130                 135                 140

Phe Lys Glu Cys Val Phe Glu Asn Tyr Tyr Val Leu Tyr Ala Ser Ala
145                 150                 155                 160

Leu Tyr Arg Gln Arg Arg Ser Gly Arg Ala Trp Tyr Leu Gly Leu Asp
                165                 170                 175

Lys Glu Gly Gln Val Met Lys Gly Asn Arg Val Lys Lys Ile Lys Ala
                180                 185                 190

Ala Ala His Phe Leu Pro Lys Leu Leu Glu Val Ala Met Tyr Gln Glu
            195                 200                 205

Pro Ser Leu His Ser Val Pro Glu Ala Ser Pro Ser Ser Pro Pro Ala
    210                 215                 220

Pro
225
```

(2) INFORMATION FOR SEQ ID NO:4:

(i) SEQUENCE CHARACTERISTICS:
        (A) LENGTH: 247 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Met Ala Ala Ile Ala Ser Gly Leu Ile Arg Gln Lys Arg Gln Ala
1               5                   10                  15

Arg Glu Gln His Trp Asp Arg Pro Ser Ala Ser Arg Arg Arg Ser Ser
            20                  25                  30

Pro Ser Lys Asn Arg Gly Leu Cys Asn Gly Asn Leu Val Asp Ile Phe
                35                  40                  45

Ser Lys Val Arg Ile Phe Gly Leu Lys Lys Arg Arg Leu Arg Arg Gln
50                  55                  60

Asp Pro Gln Leu Lys Gly Ile Val Thr Arg Leu Tyr Cys Arg Gln Gly
65                  70                  75                  80
```

```
Tyr Tyr Leu Gln Met His Pro Asp Gly Ala Leu Asp Gly Thr Lys Asp
            85                  90                  95

Asp Ser Thr Asn Ser Thr Leu Phe Asn Leu Ile Pro Val Gly Leu Arg
            100                 105                 110

Val Val Ala Ile Gln Gly Val Lys Thr Gly Leu Tyr Ile Ala Met Asn
            115                 120                 125

Gly Glu Gly Tyr Leu Tyr Pro Ser Glu Leu Phe Thr Pro Glu Cys Lys
130                 135                 140

Phe Lys Glu Ser Val Phe Glu Asn Tyr Val Ile Tyr Ser Ser Met
145                 150                 155                 160

Leu Tyr Arg Gln Gln Glu Ser Gly Arg Ala Trp Phe Leu Gly Leu Asn
            165                 170                 175

Lys Glu Gly Gln Ala Met Lys Gly Asn Arg Val Lys Lys Ile Lys Pro
            180                 185                 190

Ala Ala His Phe Leu Pro Lys Pro Leu Glu Val Ala Met Tyr Arg Glu
            195                 200                 205

Pro Ser Leu His Asp Val Gly Glu Thr Val Pro Lys Pro Gly Val Thr
            210                 215                 220

Pro Ser Lys Ser Thr Ser Ala Ser Ala Ile Met Asn Gly Gly Lys Pro
225                 230                 235                 240

Val Asn Lys Ser Lys Thr Thr
            245
```

(2) INFORMATION FOR SEQ ID NO:5:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
            85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155
```

(2) INFORMATION FOR SEQ ID NO:6:

(i) SEQUENCE CHARACTERISTICS:

(A) LENGTH: 155 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

(2) INFORMATION FOR SEQ ID NO:7:

(i) SEQUENCE CHARACTERISTICS:
        (A) LENGTH: 208 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg

```
                145                 150                 155                 160
Arg Tyr Tyr Val Ala Leu Asn Lys Asp Gly Thr Pro Arg Glu Gly Thr
                    165                 170                 175

Arg Thr Lys Arg His Gln Lys Phe Thr His Phe Leu Pro Arg Pro Val
                    180                 185                 190

Asp Pro Asp Lys Val Pro Glu Leu Tyr Lys Asp Ile Leu Ser Gln Ser
                    195                 200                 205
```

(2) INFORMATION FOR SEQ ID NO:8:

(i) SEQUENCE CHARACTERISTICS:
        (A) LENGTH: 243 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

```
Met Ala Ala Ile Ala Ser Ser Leu Ile Arg Gln Lys Arg Gln Ala
1               5                   10                  15

Arg Glu Ser Asn Ser Asp Arg Val Ala Ser Lys Arg Arg Ser Ser
                    20                  25                  30

Pro Ser Lys Asp Gly Arg Ser Leu Cys Glu Arg His Val Leu Gly Val
                    35                  40                  45

Phe Ser Lys Val Arg Phe Cys Ser Gly Arg Lys Arg Pro Val Arg Arg
    50                  55                  60

Arg Pro Glu Pro Gln Leu Lys Gly Ile Val Thr Arg Leu Phe Ser Gln
65                  70                  75                  80

Gln Gly Tyr Phe Leu Glu Met His Pro Asp Gly Thr Ile Asp Gly Thr
                    85                  90                  95

Lys Asp Glu Asn Ser Asp Tyr Thr Leu Phe Asn Leu Ile Pro Val Gly
                    100                 105                 110

Leu Arg Val Val Ala Ile Gln Gly Val Lys Ala Ser Leu Tyr Val Ala
                    115                 120                 125

Met Asn Gly Glu Gly Tyr Leu Tyr Ser Ser Asp Val Phe Thr Pro Glu
                    130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Glu Leu Gly
                    165                 170                 175

Leu Asn Lys Glu Gly Gln Ile Met Lys Gly Asn Arg Val Lys Lys Thr
                    180                 185                 190

Lys Pro Ser Ser His Phe Val Pro Lys Pro Ile Glu Val Cys Met Tyr
                    195                 200                 205

Arg Glu Pro Ser Leu His Glu Ile Gly Glu Lys Gln Gly Arg Ser Arg
                    210                 215                 220

Lys Ser Ser Gly Thr Pro Thr Met Asn Gly Gly Lys Val Val Asn Gln
225                 230                 235                 240

Asp Ser Thr
```

(2) INFORMATION FOR SEQ ID NO:9:

(i) SEQUENCE CHARACTERISTICS:
        (A) LENGTH: 245 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Met Thr Ala Ala Ile Ala Ser Ser Leu Ile Arg Gln Lys Arg Gln Ala
1               5                   10                  15

Arg Glu Arg Glu Lys Ser Asn Ala Cys Lys Cys Val Ser Ser Pro Ser
            20                  25                  30

Lys Gly Lys Thr Ser Cys Asp Lys Asn Lys Leu Asn Val Phe Ser Arg
        35                  40                  45

Val Lys Leu Phe Gly Ser Lys Lys Arg Arg Arg Arg Pro Glu Pro
50                  55                  60

Gln Leu Lys Gly Ile Val Thr Lys Leu Tyr Ser Arg Gln Gly Tyr His
65                  70                  75                  80

Leu Gln Leu Gln Ala Asp Gly Thr Ile Asp Gly Thr Lys Asp Glu Asp
                85                  90                  95

Ser Thr Tyr Thr Leu Phe Asn Leu Ile Pro Val Gly Leu Arg Val Val
            100                 105                 110

Ala Ile Gln Gly Val Gln Thr Lys Leu Tyr Leu Ala Met Asn Ser Glu
        115                 120                 125

Gly Tyr Leu Tyr Thr Ser Glu His Phe Thr Pro Glu Cys Lys Phe Lys
130                 135                 140

Glu Ser Val Phe Glu Asn Tyr Tyr Val Thr Tyr Ser Ser Met Ile Tyr
145                 150                 155                 160

Arg Gln Gln Gln Ser Gly Arg Gly Trp Tyr Leu Gly Leu Asn Lys Glu
                165                 170                 175

Gly Glu Ile Met Lys Gly Asn His Val Lys Lys Asn Lys Pro Ala Ala
            180                 185                 190

His Phe Leu Pro Lys Pro Leu Lys Val Ala Met Tyr Lys Glu Pro Ser
        195                 200                 205

Leu His Asp Leu Thr Glu Phe Ser Arg Ser Gly Ser Gly Thr Pro Thr
210                 215                 220

Lys Ser Arg Ser Val Ser Gly Val Leu Asn Gly Gly Lys Ser Met Ser
225                 230                 235                 240

His Asn Glu Ser Thr
                245
```

(2) INFORMATION FOR SEQ ID NO:10:

(i) SEQUENCE CHARACTERISTICS:
        (A) LENGTH: 225 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Met Ala Ala Leu Ala Ser Ser Leu Ile Arg Gln Lys Arg Glu Val Arg
1               5                   10                  15

Glu Pro Gly Gly Ser Arg Pro Val Ser Ala Gln Arg Arg Val Cys Pro
            20                  25                  30

Arg Gly Thr Lys Ser Leu Cys Gln Lys Gln Leu Leu Ile Leu Leu Ser
        35                  40                  45

Lys Val Arg Leu Cys Gly Gly Arg Pro Thr Arg Gln Asp Arg Gly Pro
50                  55                  60

Glu Pro Gln Leu Lys Gly Ile Val Thr Lys Leu Phe Cys Arg Gln Gly
65                  70                  75                  80
```

```
Phe Tyr Leu Gln Ala Asn Pro Asp Gly Ser Ile Gln Gly Thr Pro Glu
                85                  90                  95

Asp Thr Ser Ser Phe Thr His Phe Asn Leu Ile Pro Val Gly Leu Arg
               100                 105                 110

Val Val Thr Ile Gln Ser Ala Lys Leu Gly His Tyr Met Ala Met Asn
               115                 120                 125

Ala Glu Gly Leu Leu Tyr Ser Ser Pro His Phe Thr Ala Glu Cys Arg
130                 135                 140

Phe Lys Glu Cys Val Phe Glu Asn Tyr Tyr Val Leu Tyr Ala Ser Ala
145                 150                 155                 160

Leu Tyr Arg Gln Arg Arg Ser Gly Arg Ala Trp Tyr Leu Gly Leu Asp
               165                 170                 175

Lys Glu Gly Arg Val Met Lys Gly Asn Arg Val Lys Lys Thr Lys Ala
               180                 185                 190

Ala Ala His Phe Val Pro Lys Leu Leu Glu Val Ala Met Tyr Arg Glu
               195                 200                 205

Pro Ser Leu His Ser Val Pro Glu Thr Ser Pro Ser Ser Pro Pro Ala
210                 215                 220

His
225

(2) INFORMATION FOR SEQ ID NO:11:

(i) SEQUENCE CHARACTERISTICS:
        (A) LENGTH: 247 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Met Ala Ala Ala Ile Ala Ser Gly Leu Ile Arg Gln Lys Arg Gln Ala
1               5                  10                  15

Arg Glu Gln His Trp Asp Arg Pro Ser Ala Ser Arg Arg Arg Ser Ser
                20                  25                  30

Pro Ser Lys Asn Arg Gly Leu Phe Asn Gly Asn Leu Val Asp Ile Phe
                35                  40                  45

Ser Lys Val Arg Ile Phe Gly Leu Lys Lys Arg Arg Leu Arg Arg Gln
50                  55                  60

Asp Pro Gln Leu Lys Gly Ile Val Thr Arg Leu Tyr Cys Arg Gln Gly
65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
               100                 105                 110

Val Val Ala Ile Gln Gly Val Lys Thr Gly Leu Tyr Ile Ala Met Asn
               115                 120                 125

Gly Glu Gly Tyr Leu Tyr Pro Ser Glu Leu Phe Thr Pro Glu Cys Lys
130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
               165                 170                 175

Lys Glu Gly Gln Val Met Lys Gly Asn Arg Val Lys Lys Thr Lys Pro
               180                 185                 190

Ala Ala His Phe Leu Pro Lys Pro Leu Glu Val Ala Met Tyr Arg Glu
```

```
            195                 200                 205
Pro Ser Leu His Asp Val Gly Glu Thr Val Pro Lys Ala Gly Val Thr
    210                 215                 220

Pro Ser Lys Ser Thr Ser Ala Ser Ala Ile Met Asn Gly Gly Lys Pro
225                 230                 235                 240

Val Asn Lys Cys Lys Thr Thr
                245

(2) INFORMATION FOR SEQ ID NO:12:

(i) SEQUENCE CHARACTERISTICS:
        (A) LENGTH: 245 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

Met Gly Leu Ile Trp Leu Leu Leu Ser Leu Leu Glu Pro Ser Trp
1               5                   10                  15

Pro Thr Thr Gly Pro Gly Thr Arg Leu Arg Arg Asp Ala Gly Arg
                20                  25                  30

Gly Gly Val Tyr Glu His Leu Gly Gly Ala Pro Arg Arg Arg Lys Leu
            35                  40                  45

Tyr Cys Ala Thr Lys Tyr His Glu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Val Val Ala Ile Lys Gly Leu Phe Ser Gly Arg Tyr
                85                  90                  95

Leu Ala Met Asn Lys Arg Gly Arg Leu Tyr Ala Ser Asp His Tyr Asn
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Gly Ser Ser Gly Pro Gly Ala Gln
    130                 135                 140

Arg Gln Pro Gly Ala Gln Arg Pro Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Gly His Lys Asp His Glu Met Val Arg
                180                 185                 190

Leu Leu Gln Ser Ser Gln Pro Arg Ala Pro Gly Glu Gly Ser Gln Pro
            195                 200                 205

Arg Gln Arg Arg Gln Lys Lys Gln Ser Pro Gly Asp His Gly Lys Met
    210                 215                 220

Glu Thr Leu Ser Thr Arg Ala Thr Pro Ser Thr Gln Leu His Thr Gly
225                 230                 235                 240

Gly Leu Ala Val Ala
            245

(2) INFORMATION FOR SEQ ID NO:13:

(i) SEQUENCE CHARACTERISTICS:
        (A) LENGTH: 206 amino acids
        (B) TYPE: amino acid
        (C) STRANDEDNESS: Not Relevant
        (D) TOPOLOGY: linear
```

(ii) MOLECULE TYPE: protein (xi) SEQUENCE DESCRIPTION: SEQ ID NO:13:

```
Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Glu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
            115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Ile Phe Lys Glu Ile
145                 150                 155                 160

Leu Leu Pro Asn Asn Tyr Asn Ala Tyr Glu Ser Tyr Lys Tyr Pro Gly
                165                 170                 175

Met Glu Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
            195                 200                 205
```

(2) INFORMATION FOR SEQ ID NO:14:

(i) SEQUENCE CHARACTERISTICS:
        (A) LENGTH: 268 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

```
Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
                20                  25                  30

Gly Pro Ala Ala Thr Asp Arg Asn Pro Ile Asp Ser Ser Ser Arg Gln
            35                  40                  45

Ser Ser Ser Ser Ala Met Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
            115                 120                 125
```

```
Gly Ile Val Gly Ile Arg Gly Val Phe Ser Asn Lys Phe Leu Ala Met
        130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Pro Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

(2) INFORMATION FOR SEQ ID NO:15:

(i) SEQUENCE CHARACTERISTICS:
        (A) LENGTH: 198 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

```
Met Ser Arg Gly Ala Gly Arg Leu Gln Gly Thr Leu Trp Ala Leu Val
1               5                   10                  15

Phe Leu Gly Ile Leu Val Gly Met Val Val Pro Ser Pro Ala Gly Thr
                20                  25                  30

Arg Ala Asn Asn Thr Leu Leu Asp Ser Arg Gly Trp Gly Thr Leu Leu
            35                  40                  45

Ser Arg Ser Arg Ala Gly Leu Ala Gly Glu Ile Ala Gly Val Asn Trp
50                  55                  60

Glu Ser Gly Tyr Leu Val Gly Ile Lys Arg Gln Arg Leu Tyr Cys
65                  70                  75                  80

Asn Val Gly Ile Gly Phe His Glu Gln Val Leu Pro Asp Gly Arg Ile
                85                  90                  95

Ser Gly Thr His Glu Glu Asn Pro Tyr Ser Leu Leu Glu Ile Ser Thr
            100                 105                 110

Val Glu Arg Gly Val Val Ser Leu Phe Gly Val Arg Ser Ala Leu Glu
        115                 120                 125

Val Ala Met Asn Ser Lys Gly Arg Leu Tyr Ala Thr Pro Ser Phe Gln
130                 135                 140

Glu Glu Cys Lys Phe Arg Glu Thr Leu Leu Pro Asn Asn Tyr Asn Ala
145                 150                 155                 160

Tyr Glu Ser Asp Leu Tyr Gln Gly Thr Tyr Ile Ala Leu Ser Lys Tyr
                165                 170                 175

Gly Arg Val Lys Arg Gly Ser Lys Val Ser Pro Ile Met Thr Val Thr
            180                 185                 190

His Phe Leu Pro Arg Ile
        195
```

(2) INFORMATION FOR SEQ ID NO:16:

(i) SEQUENCE CHARACTERISTICS:
        (A) LENGTH: 194 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Leu Tyr Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr
```

(2) INFORMATION FOR SEQ ID NO:17:

(i) SEQUENCE CHARACTERISTICS:
        (A) LENGTH: 215 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

```
Met Gly Ser Pro Arg Ser Ala Leu Ser Cys Leu Leu Leu His Leu Leu
1               5                   10                  15

Val Leu Cys Leu Gln Ala Gln Val Thr Val Gln Ser Ser Pro Asn Phe
                20                  25                  30

Thr Gln His Val Arg Glu Gln Ser Leu Val Thr Asp Gln Leu Ser Arg
            35                  40                  45

Arg Leu Ile Arg Thr Tyr Gln Leu Tyr Ser Arg Thr Ser Gly Lys His
        50                  55                  60

Val Gln Val Leu Ala Asn Lys Arg Ile Asn Ala Met Ala Glu Asp Gly
65                  70                  75                  80

Asp Pro Phe Ala Lys Leu Ile Val Glu Thr Asp Thr Phe Gly Ser Arg
```

```
                       85                  90                  95
Val Arg Val Arg Gly Ala Glu Thr Gly Leu Tyr Ile Cys Met Asn Lys
                100                 105                 110
Lys Gly Lys Leu Ile Ala Lys Ser Asn Gly Lys Gly Lys Asp Cys Val
            115                 120                 125
Phe Ile Glu Ile Val Leu Glu Asn Asn Tyr Thr Ala Leu Gln Asn Ala
        130                 135                 140
Lys Tyr Glu Gly Trp Tyr Met Ala Phe Thr Arg Lys Gly Arg Pro Arg
145                 150                 155                 160
Lys Gly Ser Lys Thr Arg Gln His Gln Arg Glu Val His Phe Met Lys
                165                 170                 175
Arg Leu Pro Arg Gly His His Thr Thr Glu Gln Ser Leu Arg Phe Glu
            180                 185                 190
Phe Leu Asn Tyr Pro Pro Phe Thr Arg Ser Leu Arg Gly Ser Gln Arg
        195                 200                 205
Thr Trp Ala Pro Glu Pro Arg
    210                 215

(2) INFORMATION FOR SEQ ID NO:18:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (xi) SEQUENCE DESCRIPTION: SEQ ID NO:18:

GAATTCCGCA CACTGCGTTC GGGGTACCAA GTGGAAGGGG AAGAACGATG CCCAAAATAA      60

CAAGACGTGC CTGGGACCGC CCCGCCCCGC CCCCCGGCCG CCAGAGGTTG GGGAAGTTTA     120

CATCTGGATT TTCACACATT TTGTCGCCAC TGCCCAGACT TTGACTAACC TTGTGAGCGC     180

CGGGTTTTCG ATACTGCAGC CTCCTCAAAT TTTAGCACTG CCTCCCCGCG ACTGCCCTTT     240

CCCTGGCCGC CCAGGTCCTG CCCTCGCCCC GGCGGAGCGC AAGCCGGAGG GCGCAGTAGA     300

GGCTGGGGCC TGAGGCCCTC GCTGAGCAGC TATGGCTGCG GCGATAGCCA GCTCCTTGAT     360

CCGGCAGAAG CGGCAGGCGA GGGAGTCCAA CAGCGACCGA GTGTCGGCCT CCAAGCGCCG     420

CTCCAGCCCC AGCAAAGACG GCGCTCCCT GTGCGAGAGG CACGTCCTCG GGTGTTCAG      480

CAAAGTGCGC TTCTGCAGCG GCCGCAAGAG GCCGGTGAGG CGGAGACCAG AACCCCAGCT     540

CAAAGGGATT GTGACAAGGT TATTCAGCCA GCAGGGATAC TTCCTGCAGA TGCACCCAGA     600

TGGTACCATT GATGGGACCA AGGACGAAAA CAGCGACTAC ACTCTCTTCA ATCTAATTCC     660

CGTGGGCCTG CGTGTAGTGG CCATCCAAGG AGTGAAGGCT AGCCTCTATG TGGCCATGAA     720

TGGTGAAGGC TATCTCTACA GTTCAGATGT TTTCACTCCA GAATGCAAAT TCAAGGAATC     780

TGTGTTTGAA AACTACTATG TGATCTATTC TTCCACACTG TACCGCCAGC AAGAATCAGG     840

CCGAGCTTGG TTTCTGGGAC TCAATAAAGA AGGTCAAATT ATGAAGGGGA ACAGAGTGAA     900

GAAACCAAG CCCTCATCAC ATTTTGTACC GAAACCTATT GAAGTGTGTA TGTACAGAGA     960

ACCATCGCTA CATGAAATTG AGAAAAACA AGGGCGTTCA GGAAAAGTT CTGGAACACC     1020

AACCATGAAT GGAGGCAAAG TTGTGAATCA AGATTCAACA TAGCTGAGAA CTCTCCCCTT    1080

CTTCCCTCTC TCATCCCTTC CCCTTCCCTT CCTTCCCATT TACCCATTTC CTTCCAGTAA    1140

ATCCACCCAA GGAGAGGAAA ATAAAATGAC AACGCAAGAC CTAGTGGCTA AGATTCTGCA    1200

CTCAAAATCT TCCTTTGTGT AGGACAAGAA AATTGAACCA AAGCTTGCTT GTTGCAATGT    1260

GGTAGAAAAT TCACGTGCAC AAAGATTAGC ACACTTAAAA GCAAAGGAAA AAATAAATCA    1320
```

```
GAACTCCATA AATATTAAAC TAAACTGTAT TGTTATTAGT AGAAGGCTAA TTGTAATGAA    1380

GACATTAATA AAGATGAAAT AAACTTATTA CTTTCGGAAT TC                      1422

(2) INFORMATION FOR SEQ ID NO:19:

(i) SEQUENCE CHARACTERISTICS:
        (A) LENGTH: 1150 base pairs
        (B) TYPE: nucleic acid
        (C) STRANDEDNESS: single
        (D) TOPOLOGY: linear (xi) SEQUENCE DESCRIPTION: SEQ ID NO:19:

AATTCCGCTT GCACAGTGTC CGCCGGGCGC AGGGGCCGAC CGCACGCAGT CGCGCAGTTC      60

TGCCTCCGCC TGCCAGTCTC GCCCGCGATC CCGGCCCGGG GCTGTGGCGT CGACTCCGAC     120

CCAGGCAGCC AGCAGCCCGC GCGGGAGCCG GACCGCCGCC GGAGGAGCTC GGACGGCATG     180

CTGAGCCCCC TCCTTGGCTG AAGCCCGAGT GCGGAGAAGC CCGGGCAAAC GCAGGCTAAG     240

GAGACCAAAG CGGCGAAGTC GCGAGACAGC GGACAAGCAG CGGAGGAGAA GGAGGAGGAG     300

GCGAACCCAG AGAGGGGCAG CAAAAGAAGC GGTGGTGGTG GGCGTCGTGG CCATGGCGGC     360

GGCTATCGCC AGCTCGCTCA TCCGTCAGAA GAGGCAAGCC CGCGAGCGCG AGAAATCCAA     420

CGCCTGCAAG TGTGTCAGCA GCCCCAGCAA AGGCAAGACC AGCTGCGACA AAACAAGTT     480

AAATGTCTTT TCCCGGGTCA AACTCTTCGG CTCCAAGAAG AGGCGCAGAA GAAGACCAGA     540

GCCTCAGCTT AAGGGTATAG TTACCAAGCT ATACAGCCGA CAAGGCTACC ACTTGCAGCT     600

GCAGGCGGAT GGAACCATTG ATGGCACCAA AGATGAGGAC AGCACTTACA CTCTGTTTAA     660

CCTCATCCCT GTGGGTCTGC GAGTGGTGGC TATCCAAGGA GTTCAAACCA AGCTGTACTT     720

GGCAATGAAC AGTGAGGGAT ACTTGTACAC CTCGGAACTT TTCACACCTG AGTGCAAATT     780

CAAAGAATCA GTGTTTGAAA ATTATTATGT GACATATTCA TCAATGATAT ACCGTCAGCA     840

GCAGTCAGGC CGAGGGTGGT ATCTGGGTCT GAACAAAGAA GGAGAGATCA TGAAAGGCAA     900

CCATGTGAAG AAGAACAAGC CTGCAGCTCA TTTTCTGCCT AAACCACTGA AAGTGGCCAT     960

GTACAAGGAG CCATCACTGC ACGATCTCAC GGAGTTCTCC CGATCTGGAA GCGGGACCCC    1020

AACCAAGAGC AGAAGTGTCT CTGGCGTGCT GAACGGAGGC AAATCCATGA GCCACAATGA    1080

ATCAACGTAG CCAGTGAGGG CAAAAGAAGG GCTCTGTAAC AGAACCTTAC CTCCAGGTGC    1140

TGTTGAATTC                                                          1150

(2) INFORMATION FOR SEQ ID NO:20:

(i) SEQUENCE CHARACTERISTICS:
        (A) LENGTH: 961 base pairs
        (B) TYPE: nucleic acid
        (C) STRANDEDNESS: single
        (D) TOPOLOGY: linear (xi) SEQUENCE DESCRIPTION: SEQ ID NO:20:

GAATTCCGGC TCTTGGGGAG CCCAGCGCGC TCCGGGCGCC TGCCGGTTTG GGGGTGTCTC      60

CTCCCGGGGC GCTATGGCGG CGCTGGCCAG TAGCCTGATC CGGCAGAAGC GGGAGGTCCG     120

CGAGCCCGGG GGCAGCCGGC CGGTGTCGGC GCAGCGGCGC GTGTGTCCCC GCGGCACCAA     180

GTCCCTTTGC CAGAAGCAGC TCCTCATCCT GCTGTCCAAG GTGCGACTGT GCGGGGGGCG     240

GCCCGCGCGG CCGGACCGCG GCCCGGAGCC TCAGCTCAAA GGCATCGTCA CCAAACTGTT     300

CTGCCGCCAG GGTTTCTACC TCCAGGCGAA TCCCGACGGA AGCATCCAGG GCACCCCAGA     360

GGATACCAGC TCCTTCACCC ACTTCAACCT GATCCCTGTG GGCCTCCGTG TGGTCACCAT     420
```

```
CCAGAGCGCC AAGCTGGGTC ACTACATGGC CATGAATGCT GAGGGACTGC TCTACAGTTC        480

GCCGCATTTC ACAGCTGAGT GTCGCTTTAA GGAGTGTGTC TTTGAGAATT ACTACGTCCT        540

GTACGCCTCT GCTCTCTACC GCCAGCGTCG TTCTGGCCGG GCCTGGTACC TCGGCCTGGA        600

CAAGGAGGGC CAGGTCATGA AGGGAAACCG AGTTAAGAAG ACCAAGGCAG CTGCCCACTT        660

TCTGCCCAAG CTCCTGGAGG TGGCCATGTA CCAGGAGCCT CTCTCCACA GTGTCCCCGA         720

GGCCTCCCCT TCCAGTCCCC CTGCCCCCTG AAATGTAGTC CCTGGACTGG AGGTTCCCTG        780

CACTCCCAGT GAGCCAGCCA CCACCACAAC CTGTCTCCCA GTCCTGCTCT CACCCCTGCT        840

GCCACACACA TGCCCTGAGC AGCCAGGTCC CACTAGGTGC TCTACCCTGA GGGAGCCTAG        900

GGGCTGACTG TGACTTCCGA GGCTGCTGAG ACCCTTAGAT CTTTGGGCCT AGGAGGGAGT        960

C                                                                       961

(2) INFORMATION FOR SEQ ID NO:21:

(i) SEQUENCE CHARACTERISTICS:
        (A) LENGTH: 971 base pairs
        (B) TYPE: nucleic acid
        (C) STRANDEDNESS: single
        (D) TOPOLOGY: linear (xi) SEQUENCE DESCRIPTION: SEQ ID NO:21:

CGCCGCCTTC CCCTCCGGTG CCCCCGGCTC GCCGTCCTCC CGCGCCCTCC CTCCCCGGAC         60

CCGTTCCCGG GGCCACCATG GCCGCGGCCA TCGCTAGCGG CTTGATCCGC CAGAAGCGGC        120

AGGCGCGGGA GCAGCACTGG GACCGGCCGT CTGCCAGCAG GAGGCGGAGC AGCCCCAGCA        180

AGAACCGCGG GCTCTGCAAC GGCAACCTGG TGGATATCTT CTCCAAAGTG CGCATCTTCG        240

GCCTCAAGAA GCGCAGGTTG CGGCGCCAAG ATCCCCAGCT CAAGGGTATA GTGACCAGGT        300

TATATTGCAG GCAAGGCTAC TACTTGCAAA TGCACCCCGA TGGAGCTCTC GATGGAACCA        360

AGGATGACAG CACTAATTCT ACACTCTTCA ACCTCATACC AGTGGGACTA CGTGTTGTTG        420

CCATCCAGGG AGTGAAAACA GGGTTGTATA TAGCCATGAA TGGAGAAGGT TACCTCTACC        480

CATCAGAACT TTTTACCCCT GAATGCAAGT TTAAAGAATC TGTTTTTGAA AATTATTATG        540

TAATCTACTC ATCCATGTTG TACAGACAAC AGGAATCTGG TAGAGCCTGG TTTTTGGGAT        600

TAAATAAGGA AGGGCAAGCT ATGAAAGGGA ACAGAGTAAA GAAAACCAAA CCAGCAGCTC        660

ATTTTCTACC CAAGCCATTG GAAGTTGCCA TGTACCGAGA ACCATCTTTG CATGATGTTG        720

GGGAAACGGT CCCGAAGCCT GGGGTGACGC CAAGTAAAAG CACAAGTGCG TCTGCAATAA        780

TGAATGGAGG CAAACCAGTC AACAAGAGTA AGACAACATA GCCAGATCCT CACAGGTGTT        840

GTGACTTATT CGTCCTGAGC ACAGTTGAGT GATTTATCCT CACCAGACAT TCCTGCTCCG        900

TGGCTGAAGA GCAGCAGGAA GTAAGCTAAT GCTTATTCTT TGCTGTCTCC GAACTTCTCT        960

GTTGCAAGTG G                                                            971

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 4 is Isoleucine or
            Leucine; Xaa in position 7 is Serine or Glycine.
```

(xi) SEQUENCE DESCRIPTION: SEQ ID NO:22:

Ala Ala Ala Xaa Ala Ser Xaa Ser Leu Ile Arg Gln Lys Arg
1               5                   10

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 9 is Arginine or
            Lysine.

(xi) SEQUENCE DESCRIPTION: SEQ ID NO:23:

Pro Gln Leu Lys Gly Ile Val Thr Xaa
1               5

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 2 is Leucine or
            Histidine.

(xi) SEQUENCE DESCRIPTION: SEQ ID NO:24:

Thr Xaa Phe Asn Leu Ile Pro Val Gly Leu Arg Val Val
1               5                   10

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 4 is Glycine, Serine,
            or Alanine; Xaa in position 7 is Tyrosine or Leucine.

(xi) SEQUENCE DESCRIPTION: SEQ ID NO:25:

Ala Met Asn Xaa Glu Gly Xaa Leu Tyr
1               5

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 3 is Serine or
            Cysteine.

(xi) SEQUENCE DESCRIPTION: SEQ ID NO:26:

Lys Glu Xaa Val Phe Glu Asn Tyr Tyr Val
1               5                   10

(2) INFORMATION FOR SEQ ID NO:27:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:27:

Val Phe Glu Asn Tyr Tyr Val
1               5

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 4 is Alanine or
            Glycine; Xaa in position 6 is Phenylalanine or
            Tyrosine.

(xi) SEQUENCE DESCRIPTION: SEQ ID NO:28:

Ser Gly Arg Xaa Trp Xaa Leu Gly Leu
1               5

(2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 5 is Arginine or
            Histidine; Xaa in position 9 is Threonine or Asparagine.

(xi) SEQUENCE DESCRIPTION: SEQ ID NO:29:

Met Lys Gly Asn Xaa Val Lys Lys Xaa Lys
1               5                   10

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 5 is Histidine or
            Arginine.

(xi) SEQUENCE DESCRIPTION: SEQ ID NO:30:

```
Met Lys Gly Asn Xaa Val Lys
1               5
```

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa in position 2 is Cysteine or
            Alanine; Xaa in position 5 is Arginine, Glutamine,
            or Lysine.

(xi) SEQUENCE DESCRIPTION: SEQ ID NO:31:

```
Val Xaa Met Tyr Xaa Glu Pro Ser Leu His
1               5                   10
```

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

GACGAGATAT TAGAATTCTA CTCGNNNNNN                          30

(2) INFORMATION FOR SEQ ID NO:33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:33:

CCCCCCCCCG ACGAGATATT AGAATTCTAC TCG                     33

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:34:

CCGATCGAAT TCGTNTTYGA RAAYTAYTAY GT                       32

(2) INFORMATION FOR SEQ ID NO:35:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:35:

GCGATCGGAT CCTTNACRTG RTTNCCYTTC AT                       32

(2) INFORMATION FOR SEQ ID NO:36:

(i) SEQUENCE CHARACTERISTICS:

```
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:36:

GCGATCGGAT CCTTNACYCT RTTNCCYTTC AT                             32

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:37:

GCGATCGGAT CCTTNACNCG RTTNCCYTTC AT                             32
```